United States Patent
Cicero et al.

(10) Patent No.: US 10,739,299 B2
(45) Date of Patent: Aug. 11, 2020

(54) NANOPORE WELL STRUCTURES AND METHODS

(71) Applicant: Roche Sequencing Solutions, Inc., Pleasanton, CA (US)

(72) Inventors: Ronald L. Cicero, Pleasanton, CA (US); Kenneth A. Honer, Santa Clara, CA (US); John Foster, Mountain View, CA (US); Pirooz Parvarandeh, Pleasanton, CA (US); Marowen Ng, San Jose, CA (US); Wing Au, San Jose, CA (US); Guojun Chen, Ventura, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 233 days.

(21) Appl. No.: 15/920,158

(22) Filed: Mar. 13, 2018

(65) Prior Publication Data
US 2018/0266980 A1 Sep. 20, 2018

Related U.S. Application Data

(60) Provisional application No. 62/471,309, filed on Mar. 14, 2017, provisional application No. 62/577,089, filed on Oct. 25, 2017.

(51) Int. Cl.
*G01N 33/487* (2006.01)
*G01N 27/327* (2006.01)
(Continued)

(52) U.S. Cl.
CPC .... *G01N 27/3278* (2013.01); *B01L 3/502707* (2013.01); *C12Q 1/6869* (2013.01);
(Continued)

(58) Field of Classification Search
CPC .......... G01N 27/3277; G01N 27/3278; G01N 33/48721; G01N 15/12; G01N 15/1218;
(Continued)

(56) References Cited

U.S. PATENT DOCUMENTS 5,187,096 A * 2/1993 Giaever ............. G01N 33/4836
204/403.01
9,322,062 B2 4/2016 Davis et al.
(Continued)

FOREIGN PATENT DOCUMENTS

WO 2006104639 2/2007
WO 2013188841 12/2013
WO 2017/070549 A1 4/2017

OTHER PUBLICATIONS

International Search Report and Written Opinion dated Oct. 9, 2018 in corresponding PCT/EP2018/056316, filed on Mar. 14, 2018, pp. 1-14.

*Primary Examiner* — James Lin
*Assistant Examiner* — Vivian A Tran
(74) *Attorney, Agent, or Firm* — Roche Sequencing Solutions, Inc.

(57) ABSTRACT

A nanopore cell may include a well having a working electrode at a bottom of the well. The well may be formed within a dielectric layer, where the sidewalls of the well may be formed of the dielectric or other materials coating the walls of the dielectric layer. Various materials having different hydrophobicity and hydrophilicity can be used to provide desired properties of the cell. The nanopore in the nanopore cell can be inserted in a membrane formed over the well. Various techniques can be used for providing a desired shape and other properties e.g., of materials and processes for forming the well.

8 Claims, 27 Drawing Sheets

(51) Int. Cl.
*B01L 3/00* (2006.01)
*C12Q 1/6869* (2018.01)

(52) U.S. Cl.
CPC ... *G01N 27/3277* (2013.01); *G01N 33/48721* (2013.01); *C12Q 2565/631* (2013.01)

(58) Field of Classification Search
CPC .......... G01N 15/1245; G01N 15/1254; G01N 15/1209; C12Q 1/6869; C12Q 2565/631; B01L 3/502707; B01L 3/5027
See application file for complete search history.

(56) References Cited

U.S. PATENT DOCUMENTS

| | | | |
|---|---|---|---|
| 2010/0155687 A1* | 6/2010 | Reyes | H01L 45/04 257/4 |
| 2012/0122715 A1* | 5/2012 | Gao | G01N 33/5438 506/9 |
| 2015/0153302 A1* | 6/2015 | Davis | G01N 27/3277 204/403.08 |
| 2016/0216233 A1* | 7/2016 | Hovis | G01N 33/48721 |
| 2016/0245789 A1* | 8/2016 | Ikeda | G01N 33/48721 |
| 2017/0037467 A1 | 2/2017 | Foster et al. | |
| 2017/0058397 A1 | 3/2017 | Mager et al. | |
| 2017/0059546 A1* | 3/2017 | Foster | G01N 33/48721 |
| 2018/0088072 A1 | 3/2018 | Yakushenko | |

* cited by examiner

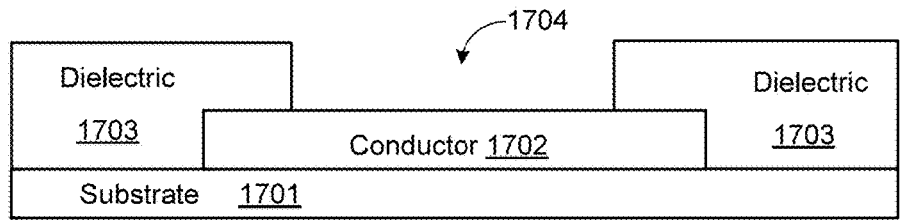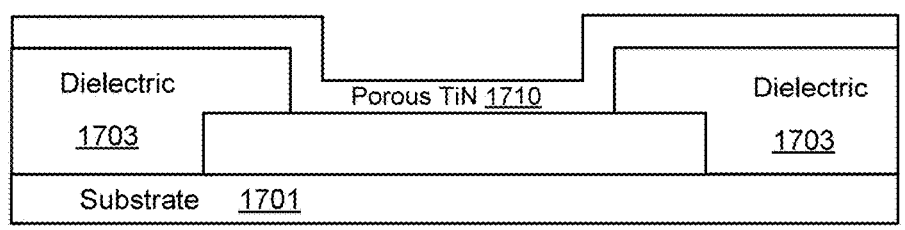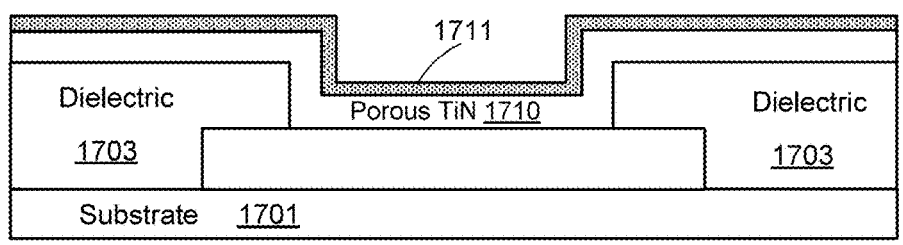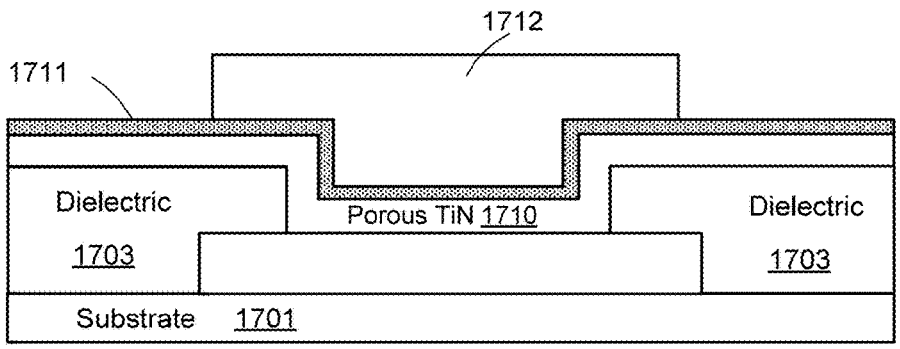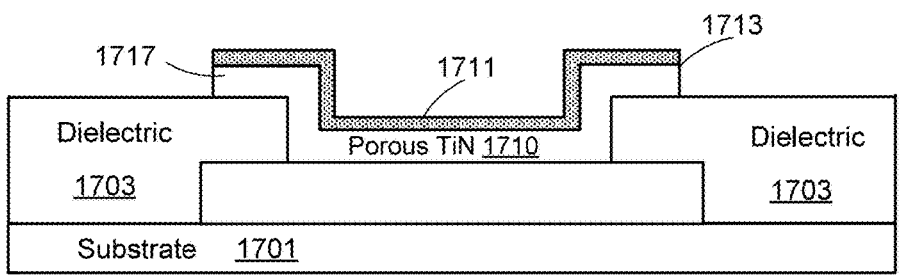

NANOPORE WELL STRUCTURES AND METHODS

CROSS-REFERENCES TO RELATED APPLICATIONS

This application claims the benefit of priority to U.S. Provisional Application Nos. 62/471,309, filed Mar. 14, 2017 and 62/577,089, filed Oct. 25, 2017, the disclosures of which are incorporated by reference herein.

BACKGROUND

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can exist. The size of the current is sensitive to the pore size and which molecule is in the nanopore. The molecule can be a nucleotide itself (e.g., as part of a nucleic acid) or a particular tag attached to a particular nucleotide, thereby allowing detection of a nucleotide at a particular position of a nucleic acid. A voltage in a circuit including the nanopore can be measured (e.g., at an integrating capacitor) as a way of measuring the resistance of the molecule, thereby allowing detection of which molecule is in the nanopore.

Even though nanopore-based sequencing sensor chips have been successful in some applications, improvements are still desirable. For example, there is a need for improved nanopore well structures and methods.

BRIEF SUMMARY

Embodiments are directed to nanopore cells that include a well having a working electrode at a bottom of the well. The well may be formed within a dielectric layer, where the sidewalls of the well may be formed of the dielectric or other materials coating the walls of the dielectric layer. Various embodiments may use different materials having different hydrophobicity and hydrophilicity to provide desired properties of the cell. In operation, the nanopore cell may have a membrane formed over the well, where the nanopore can be inserted into the membrane. A shape of the well can impact the properties and ability to form the membrane, which can further impact the ease of performing measurements with the nanopore cell. Various techniques can be used for providing a desired shape and other properties (e.g., of materials forming the well).

According to some embodiments, a nanopore cell may include a substrate, a conductive layer disposed overlying a top portion of the substrate, and a first dielectric layer overlying the conductive layer. The first dielectric layer can have an opening exposing a portion of the conductive layer. An electrode layer maybe disposed in the opening of the first dielectric layer. The electrode layer may have an overhang portion extending over the first dielectric layer. Further, a second dielectric layer is disposed on the first dielectric layer, and a cavity is formed in the second dielectric layer. The cavity exposes a portion of the electrode layer. Further, the cavity may include an undercut portion of the second dielectric layer above the overhang portion of the electrode. The nanopore device can include a well formed by the cavity. The well has a bottom base formed by a top surface of the electrode layer and well sidewalls formed by the second dielectric layer.

According to an embodiment, a shape of the well can include aspects of a corner between a top surface of the dielectric layer and the well sidewall. The corner can be characterized by a radius of curvature r, and an angle between the top surface of the dielectric layer and the well sidewall is characterized by an angle θ. The values for the curvature r and angle θ can be selected to provide desired properties of the well, thereby providing desired properties of the nanopore cell.

Embodiments may include a nanopore cell that includes a substrate, a conductive layer disposed in a top portion of the substrate, an electrode layer disposed on the conductive layer, and a dielectric layer disposed on the electrode layer. The nanopore cell also includes a cavity formed in the dielectric layer and exposes a portion of the electrode layer. Further, a well is formed in the cavity, and the well has a well sidewall formed by the dielectric layer and a well bottom on the exposed portion of the electrode layer. A corner between a top surface of the dielectric layer and the well sidewall can be characterized by a radius of curvature r, and an angle between the top surface of the dielectric layer and the well sidewall can be characterized by an angle θ.

Some embodiments may include a method for forming a nanopore cell. The method may include providing a device structure having a conductive layer disposed in a top portion of a substrate and a porous TiN electrode layer disposed on the conductive layer and surrounded by an oxide layer. The method includes forming a buffer layer on the oxide layer, forming a polyimide layer on the oxide buffer layer, removing a portion of the polyimide layer to form a cavity to expose a portion of the oxide buffer layer, and removing the exposed portion of the oxide buffer layer to expose a portion of the porous TiN electrode layer to form a well. The well includes a bottom base formed by a top surface of the porous electrode layer and well sidewalls of the stacked polyimide layer over the oxide buffer layer. The porous TiN electrode layer is prevented from contacting the polyimide layer during the formation of the well.

Some embodiments may include a method for forming a nanopore cell. The nanopore includes providing a substrate including a conductive layer disposed in a top portion of the substrate and a porous electrode layer disposed on the conductive layer surrounded by a first dielectric layer. The method also includes forming a second dielectric layer on the first dielectric layer, forming a third dielectric layer on the second dielectric layer, removing a portion of the third dielectric layer to form a cavity to expose a portion of the second dielectric layer, and removing the exposed portion of the second dielectric layer to expose a portion of the porous electrode layer to form a well. The well includes a bottom base formed by a top surface of the electrode layer and well sidewalls of the stacked third dielectric layer over the second dielectric layer. The porous electrode layer is prevented from contacting the third dielectric layer during the formation of the well.

Some embodiments may include a nanopore cell that includes a substrate, a conductive layer disposed in a top portion of the substrate, a porous titanium nitride (TiN) electrode layer disposed on the conductive layer, a first dielectric layer disposed on the porous TiN electrode layer, and a polyimide layer disposed on the first dielectric layer. A cavity is formed in the polyimide layer and the first dielectric layer, and the cavity exposes a portion of the porous TiN electrode layer. A well is formed by the cavity on the exposed portion of the porous TiN electrode layer, and the well has a bottom base formed by a top surface of the porous TiN electrode layer and well sidewalls of the stacked polyimide layer over the first dielectric layer.

Some embodiments may include a method for forming a nanopore cell. The method includes providing a substrate having a conductive layer disposed in a top portion of the substrate, forming a porous titanium nitride (TiN) electrode layer on the conductive layer, forming a sacrificial dielectric layer on the TiN electrode layer, patterning a sacrificial dielectric layer to form a sacrificial structure having a base that is wider than its top surface. The method also includes forming a polyimide layer over the porous TiN electrode and surrounding the sacrificial structure and removing the sacrificial structure to form a well that includes a bottom base of the porous TiN electrode layer and well sidewalls of polyimide. Further, the polyimide sidewalls have a reentrant profile.

Some embodiments may include a method for forming a nanopore cell. The method includes providing a substrate having a conductive layer disposed in a top portion of the substrate, forming an electrode layer on the conductive layer, forming a first dielectric layer on the electrode layer, patterning a first dielectric layer to form a sacrificial structure having a base that is wider than its top surface, forming a second dielectric layer over the electrode surrounding the sacrificial structure, and removing the sacrificial structure to form a well that includes a bottom base of the electrode layer and well sidewalls of the second dielectric layer, the well sidewalls having a reentrant profile.

Some embodiments may include a nanopore cell. The nanopore cell includes a substrate, a conductive layer disposed in a top portion of the substrate, a porous titanium nitride (TiN) electrode layer disposed on the conductive layer, a polyimide layer disposed on the porous titanium nitride (TiN) electrode layer. The nanopore cell also includes a cavity in the polyimide layer, and the cavity exposes a portion of the TiN electrode layer. Further, a well is formed by the cavity on the exposed portion of the TiN electrode layer. The well has a bottom base of the TiN electrode layer and well sidewalls of the polyimide layer. Further, the polyimide sidewalls have a reentrant profile.

Some embodiments may include a nanopore cell includes a substrate, a conductive layer disposed in a top portion of the substrate, an electrode layer disposed on the conductive layer, a dielectric layer disposed on the electrode layer. A cavity in the dielectric layer, and the cavity exposes a portion of the electrode layer. A well is formed by the cavity on the exposed portion of the electrode layer, and the well has the exposed portion of the electrode layer as a bottom base and sidewalls extending from a top opening to the bottom base forming a reentrant profile. Further, the bottom base is wider than the top opening.

Some embodiments may include another method for forming a nanopore cell. The method can include providing a device structure that has a conductive layer disposed in a top portion of a substrate and a first dielectric layer surrounding the conductive layer. The first dielectric layer includes an opening that exposes a portion of the conductive layer. The method includes forming a porous electrode layer overlying the exposed portion of the conductive layer and the first dielectric layer. A sacrificial layer is formed overlying the porous electrode layer. The method also includes patterning the sacrificial layer and the porous electrode layer to form a stacked layer covering the opening in the first dielectric layer. Next, a second dielectric layer is formed on the stacked layer and the first dielectric layer. The method also includes removing a portion of the second dielectric layer to form a cavity to expose the sacrificial layer of the stacked layer. The method further includes removing the sacrificial layer to expose a portion of the porous electrode layer to form a well with the second dielectric layer. The well includes a bottom base and well sidewalls, the bottom base being formed by a top surface of the porous electrode layer and the well sidewalls being formed by the second dielectric layer. The porous electrode layer is prevented from contacting the second dielectric layer during formation of the well. The sacrificial layer can a metal layer or a dielectric layer. In some embodiments, the sacrificial layer is a titanium (Ti) layer. The second dielectric layer can be a polyimide layer.

A better understanding of the nature and advantages of embodiments of the present invention may be gained with reference to the following detailed description and the accompanying drawings.

BRIEF DESCRIPTION OF THE DRAWINGS

FIGS. 17A-17H illustrate a process for constructing an electrochemical cell of a nanopore-based sequencing chip without using a polishing method.

TERMS

Figure 1:
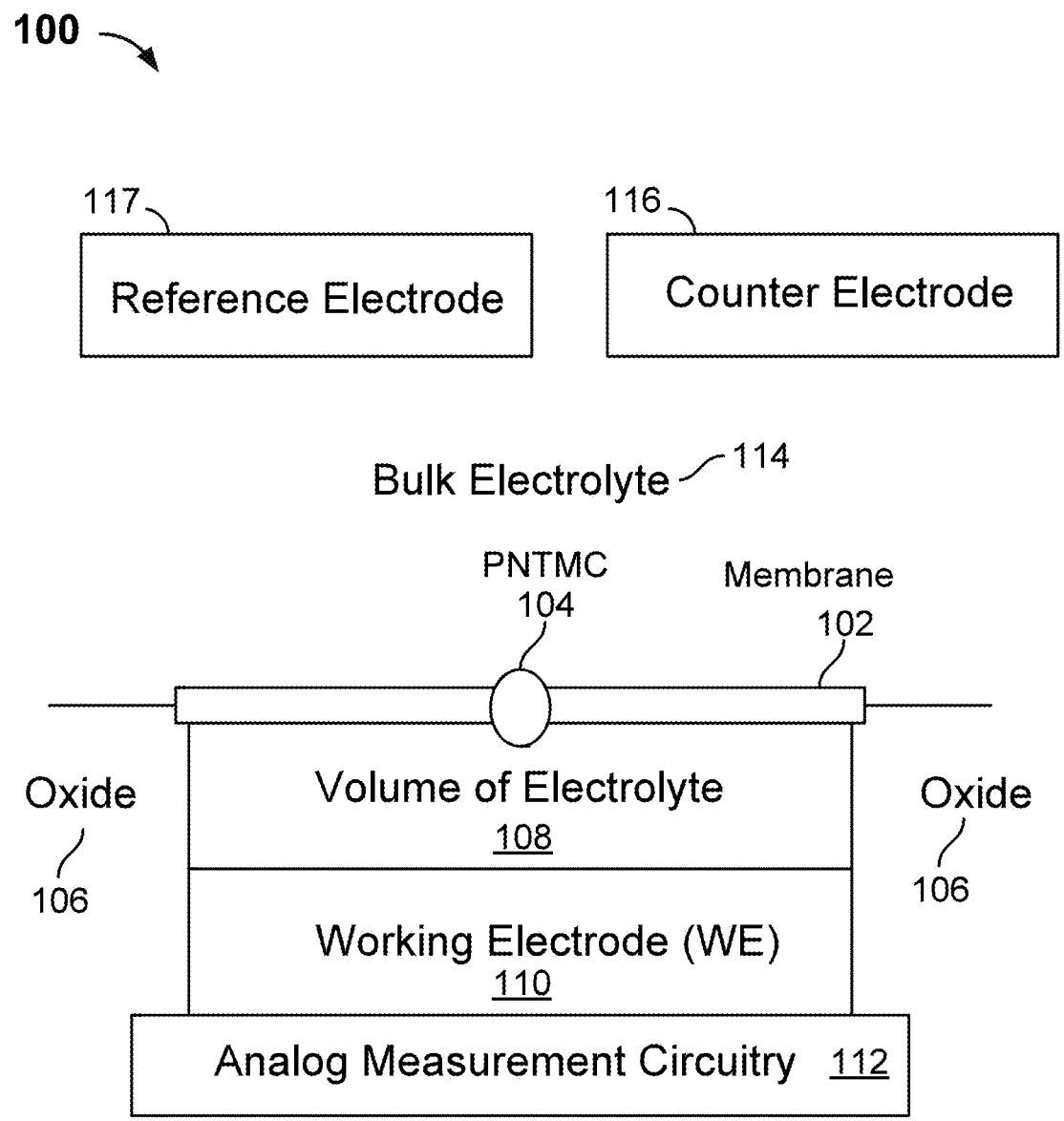
FIG. 1 illustrates an embodiment of a cell in a nanopore-based sequencing chip.

A "nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

A "well" in a nanopore device refers to a structure formed by insulating walls and a working electrode into which an electrolyte may be contained. A "well profile" refers to a structural description of the well and can include measures of an angle and a sharpness of a well edge. A "cell" of a nanopore device can include at various stages of operation: a well, a nanopore (e.g., in a membrane across the well), and a working electrode, as well as other circuitry, e.g., data acquisition circuitry.

A "dielectric material" refers to an electrical insulator that can be polarized by an applied electric field. When a dielectric is placed in an electric field, electric charges do not flow through the material as they do in a conductor, but only slightly shift from their average equilibrium positions causing dielectric polarization. A "conductive layer" refers to a layer of material that allows the flow of an electrical current in one or more directions. A metal wire is a common electrical conductor.

A "porous material" refers to a material that contains pores or voids at a surface of the material. A "spongy material" refers to a material having an open, porous structure.

DETAILED DESCRIPTION

In a nanopore device, a membrane can be formed over a well in a dielectric layer. For example, the membrane can include a lipid monolayer formed on top of the dielectric layer. As the membrane reaches the opening of well, the lipid monolayer can transition to a lipid bilayer that spans across the opening of the well. The shape of the well and the materials that form the well can perform important roles in the formation of the membrane and the insertion of the nanopore in the membrane. Further, the interaction between the materials forming the well can also affect the operation of the nanopore device.

The description below includes an overview of a structure and operation of nanopore cells. The impact of the shape of the well and the materials that form the well are also discussed. The problems caused by the interaction between a porous dielectric material and a porous working electrode are also described, along with proposed solutions.

I. Overview of Nanopore Cells

This section includes an introduction to the operation of a nanopore cell, cell structure and usage, and circuitry for measuring signal. The capacitive effects at a working electrode (referred to as a double layer capacitance) are explained, and an example process of constructing a porous working electrode for improving the measurement is described.

A. Operation of the Cell

FIG. 1 illustrates an embodiment of a cell 100 in an array of cells that form a nanopore-based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest (e.g., a single polymer molecule, such as DNA) can be placed directly onto the surface of the cell. A single PNTMC 104 can be inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 can modulate the ionic current through the otherwise impermeable bilayer.

Analog measurement circuitry 112 is connected to a working electrode 110 (e.g., made of metal) covered by a volume of electrolyte 108 inside a well formed in an oxide layer 106. The volume of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116. The cell also includes a reference electrode 117, which can act as an electrochemical potential sensor.

Figure 2:
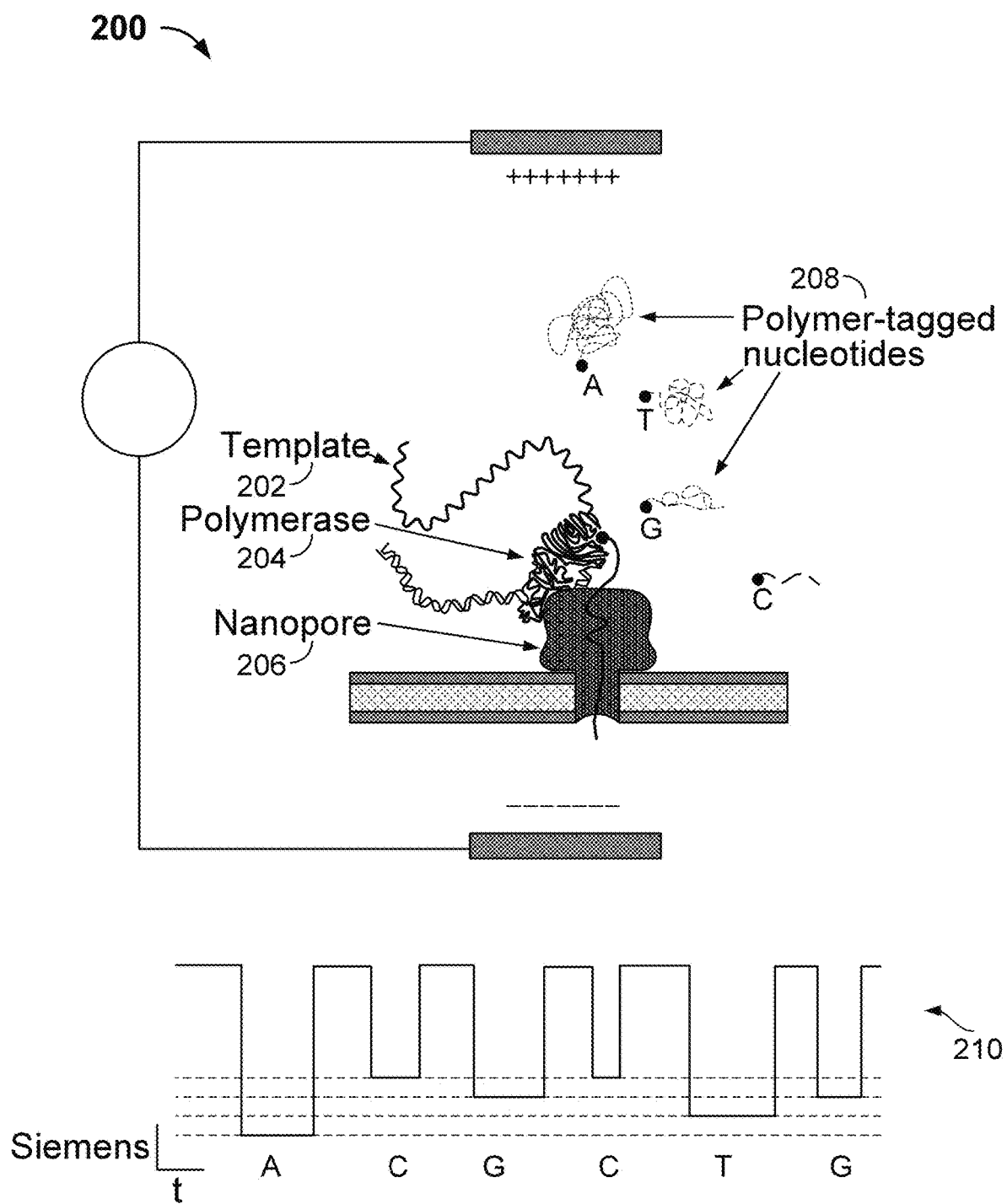
FIG. 2 illustrates an embodiment of a cell performing nucleotide sequencing with the Nano-SBS technique.

FIG. 2 illustrates an embodiment of a cell 200 performing nucleotide sequencing with the nanopore-based sequencing by a synthesis (Nano-SBS) technique. In the Nano-SBS technique, a template 202 to be sequenced and a primer are introduced to cell 200. To this template-primer complex, four differently tagged nucleotides 208, A, T, G, and C are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

B. Cell Structure and Usage

Figure 3:
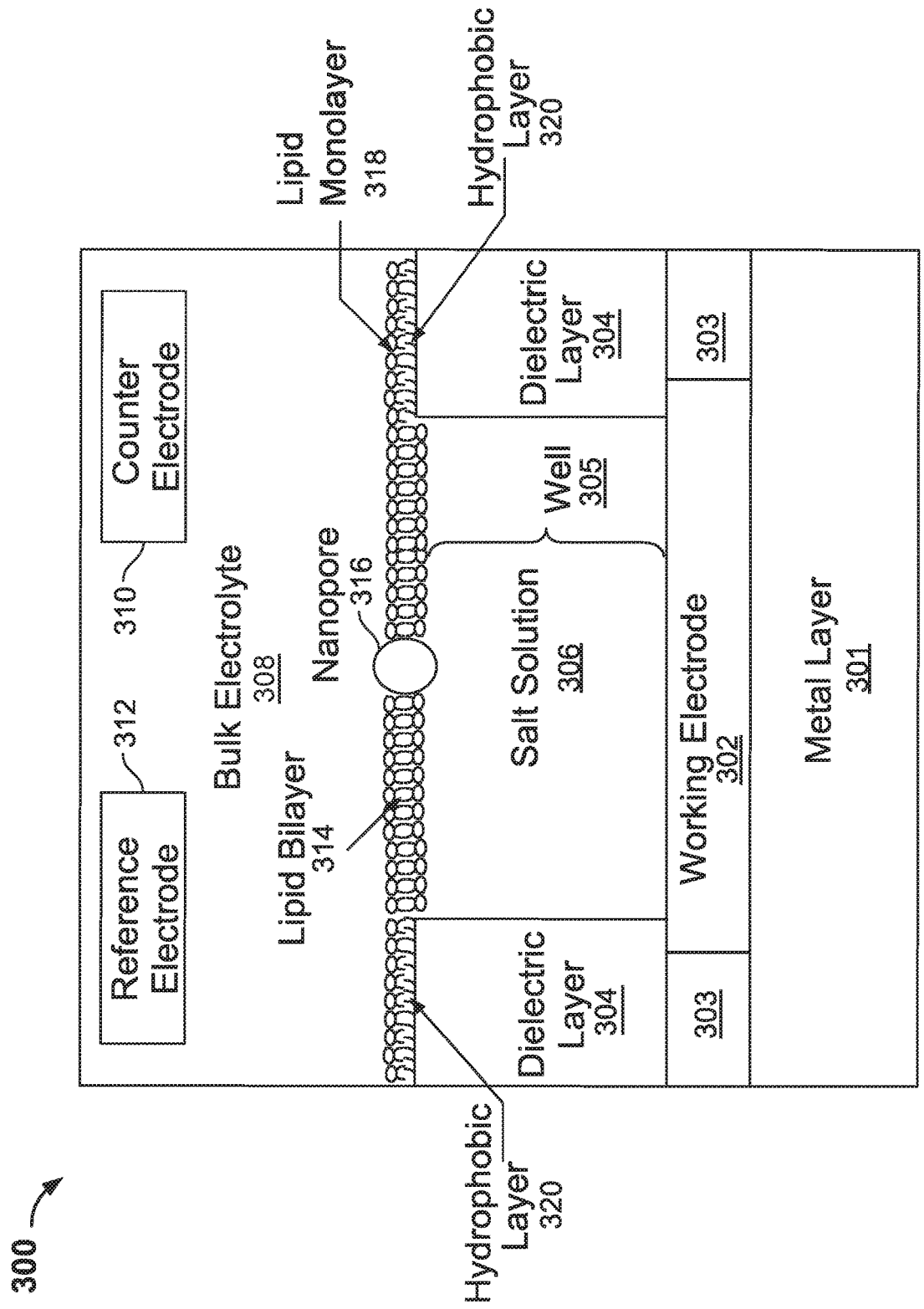
FIG. 3 illustrates an embodiment of an electrochemical cell of a nanopore-based sequencing chip that includes a TiN working electrode with increased electrochemical capacitance.

FIG. 3 illustrates an embodiment of electrochemical cell 300 of a nanopore-based sequencing chip that includes a working electrode (e.g., TiN, which has a high electrochemical capacitance). Cell 300 includes a conductive or metal layer 301. Metal layer 301 connects cell 300 to the remaining portions of the nanopore-based sequencing chip. In some embodiments, metal layer 301 is the top metal of the CMOS chip (e.g., metal 6 layer M6 of the underlying circuitry). Cell 300 further includes a working electrode 302 and a dielectric layer 303 above metal layer 301. In some embodiments, working electrode 302 can be circular or octagonal in shape, and dielectric layer 303 forms the walls surrounding working electrode 302. Cell 300 further includes a dielectric layer 304 above working electrode 302 and dielectric layer 303. Dielectric layer 304 forms the insulating walls surrounding a well 305.

In some embodiments, dielectric layer 303 and dielectric layer 304 together form a single piece of dielectric. Dielectric layer 303 is the portion that is disposed horizontally adjacent to working electrode 302, and dielectric layer 304 is the portion that is disposed above and covering a portion of the working electrode. In some embodiments, dielectric layer 303 and dielectric layer 304 are separate pieces of dielectric and they may be formed separately. Well 305 has an opening above an uncovered portion of the working electrode. In some embodiments, the opening above the uncovered portion of the working electrode can be circular or octagonal in shape.

Inside well 305, a volume of salt solution/electrolyte 306 is disposed above working electrode 302. Salt solution 306 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaClz), strontium chloride (SrClz), manganese chloride (MnClz), and magnesium chloride (MgClz). In some embodiments, salt solution 306 has a thickness of about three microns (μm). The thickness of salt solution 306 may range from 0-5 microns.

The dielectric material used to form dielectric layers 303 and 304 includes glass, oxide, silicon mononitride (SiN), and the like. The top surface of dielectric layer 304 may be silanized. Silanization forms a hydrophobic layer 320 above the top surface of dielectric layer 304. In some embodiments, hydrophobic layer 320 has a thickness of about 1.5 nanometers (nm). Alternatively, dielectric material that is hydrophobic such as hafnium oxide may be used to form dielectric layer 304.

As shown in FIG. 3, a membrane is formed on top of dielectric layer 304 and spans across well 305. For example, the membrane includes a lipid monolayer 318 formed on top of hydrophobic layer 320 and as the membrane reaches the opening of well 305, the lipid monolayer transitions to a lipid bilayer 314 that spans across the opening of the well. Hydrophobic layer 320 facilitates the formation of lipid monolayer 318 above dielectric layer 304 and the transition from a lipid monolayer to a lipid bilayer. A bulk electrolyte 308 containing protein nanopore transmembrane molecular complexes (PNTMC) and the analyte of interest is placed directly above the well. A single PNTMC/nanopore 316 is inserted into lipid bilayer 314 by electroporation. Nanopore 316 crosses lipid bilayer 314 and provides the only path for ionic flow from bulk electrolyte 308 to working electrode 302. Bulk electrolyte 308 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCb), strontium chloride (SrCb), manganese chloride (MnCb), and magnesium chloride (MgCb).

Cell 300 includes a counter electrode (CE) 310. Cell 300 also includes a reference electrode 312, which acts as an electrochemical potential sensor. In some embodiments, counter electrode 300 can be shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

Working electrode 302 is a titanium nitride (TiN) working electrode with increased electrochemical capacitance. The electrochemical capacitance associated with working electrode 302 may be increased by maximizing the specific surface area of the electrode. The specific surface area of working electrode 302 is the total surface area of the electrode per unit of mass (e.g., $m^2/kg$) or per unit of volume (e.g., $m^2/m^3$, $m^2/m^3$, or $m^{-1}$ or per unit of base area (e.g., $m^2/m^2$). As the surface area increases, the electrochemical capacitance of the working electrode increases, and a greater amount of ions can be displaced with the same applied potential before the capacitor becomes charged. The surface area of working electrode 302 may be increased by making the TiN electrode "spongy" or porous. The TiN sponge soaks up electrolyte and creates a large effective surface area in contact with the electrolyte.

The ratio of the capacitance associated with the membrane $C_{membrane}$ and the capacitance associated with the working electrode $C_{electrochemical}$ may be adjusted to achieve optimal overall system performance. Increased system performance may be achieved by reducing $C_{membrane}$ while maximizing $C_{electrochemical}$. $C_{membrane}$ can be adjusted to create the required RC time constant without the need for additional on-chip capacitance, thereby allowing a significant reduction in cell size and chip size.

In cell 300, the base surface area of the opening of well 305 (which is the same as the base surface area of lipid bilayer 314) and the base surface area of working electrode 302 are determined by the dimensions of dielectric layer 304 and dielectric layer 303, respectively. The base surface area of working electrode 302 is greater than or equal to the base surface area of the opening of well 305. Therefore, the two base surface areas may be optimized independently to provide the desired ratio between $C_{membrane}$ and $C_{electrochemical}$. As shown in FIG. 3, a portion of working electrode 302 is covered by dielectric 304 and therefore the covered portion does not have direct contact with salt solution/electrolyte 306. By using a spongy and porous TiN working electrode, the electrolyte can diffuse through the spaces between the columnar TiN structures and vertically down the uncovered portion of the working electrode and then horizontally to the covered portion of working electrode 302 that is underneath dielectric layer 304. As a result, the effective surface area of TiN that is in contact with the electrolyte is maximized and $C_{electrochemical}$ is maximized.

C. Circuitry for Measuring Signal

Figure 4:
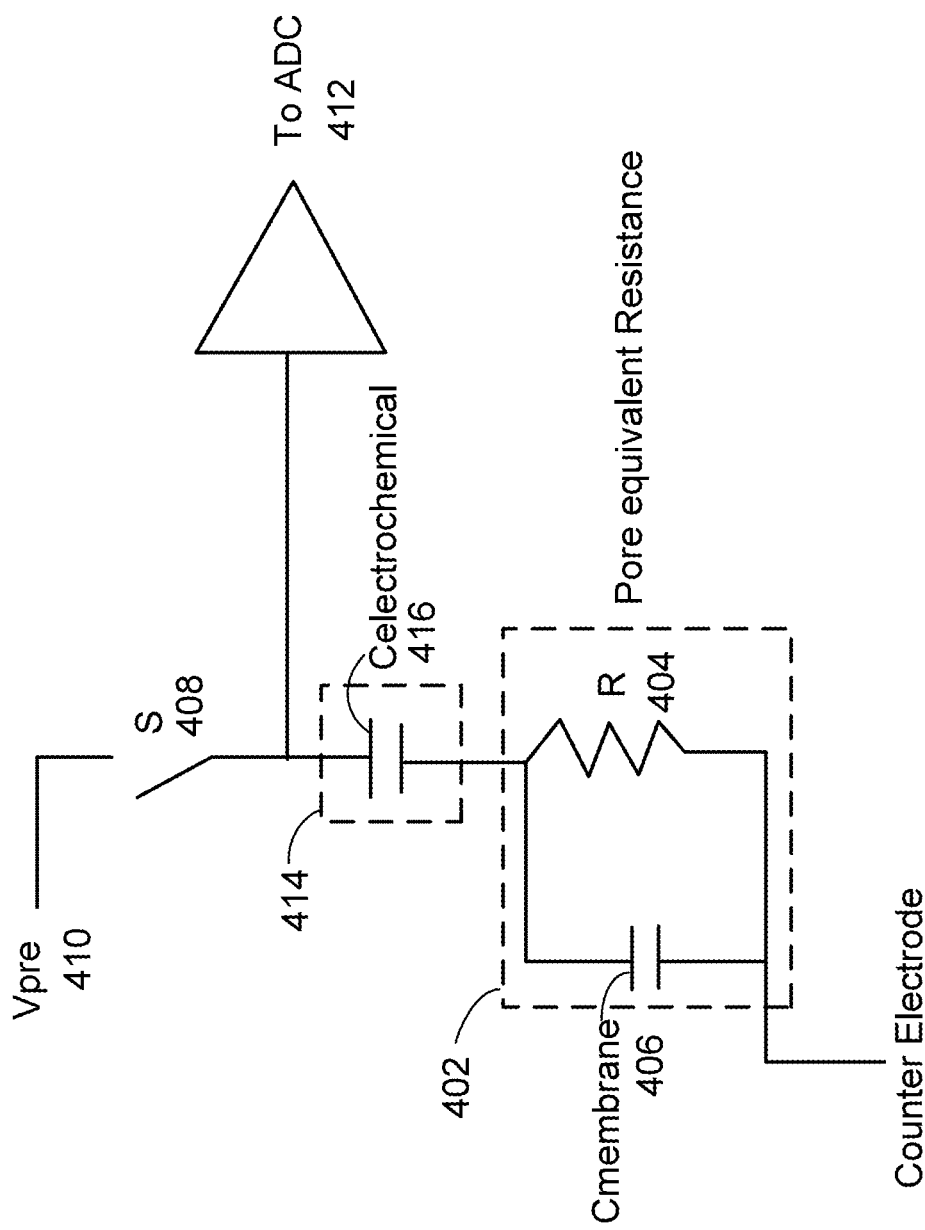
FIG. 4 illustrates an additional embodiment of a circuitry in a cell of a nanopore-based sequencing chip, wherein the voltage applied across the nanopore can be configured to vary over a time period during which the nanopore is in a particular detectable state.

FIG. 4 illustrates an embodiment of a circuitry 400 in a cell of a nanopore-based sequencing chip, wherein the voltage or current applied across the nanopore can be configured to vary over a time period during which the nanopore is in a particular detectable state. In FIG. 4, instead of showing a nanopore inserted in a membrane and the liquid surrounding the nanopore, an electrical model 402 represents the electrical properties of the nanopore and the membrane, and an electrical model 414 represents the electrical properties of the working electrode are shown.

Electrical model 402 includes a capacitor 406 that models a capacitance associated with the membrane ($C_{membrane}$) and a resistor 404 that models a resistance associated with the nanopore in different states (e.g., the open-channel state or the states corresponding to having different types of tags or molecules inside the nanopore). Electrical model 414 includes a capacitor 416 that models a capacitance associated with the working electrode. The capacitance associated with the working electrode is also referred to as an electrochemical capacitance ($C_{electrochemical}$). The electrochemical capacitance $C_{electrochemical}$ associated with the working electrode includes a double-layer capacitance and may further include a pseudo capacitance.

FIG. 4 also includes a switch 408 coupled to a voltage 410, which can be switched on and off for the purpose of measuring resistance 404. In some embodiments, voltage 410 is applied to electrical model 402 representing the nanopore. After capacitor 406 is fully charged (which may not be very long as it is desirable for the membrane to have a low capacitance), the switch 408 can be opened, and current can flow from one side of capacitor 406 to the other side via resistor 404 (i.e., the nanopore that includes the molecule being detected). Different values for resistor 404 will cause different current to flow, and thus different voltage decays. Capacitor 416 can be sufficiently large to not impact the circuit significantly.

After a specified amount of time, a voltage can be measured at an ADC (Analog-to-Digital Converter) 412. This can measure the time constant in the circuit represented by $RC_{membrane}$, as the voltage changes after the specified amount of time will correlate to the resistance of the pore (and thus the molecule inside of it). Embodiments can also measure an amount of time to reach a specific voltage, e.g., by using a comparator, as is described in U.S. Pat. No. 9,377,437.

D. Capacitive Effects at Working Electrode (Double Layer Capacitance)

It is desirable for the working electrode to have a high capacitance, thereby reducing its impedance effect on the circuit, which can cause voltage levels to move slightly as a result of charge build up after multiple measurements that involve switch 408 opening and closing.

Figure 5:
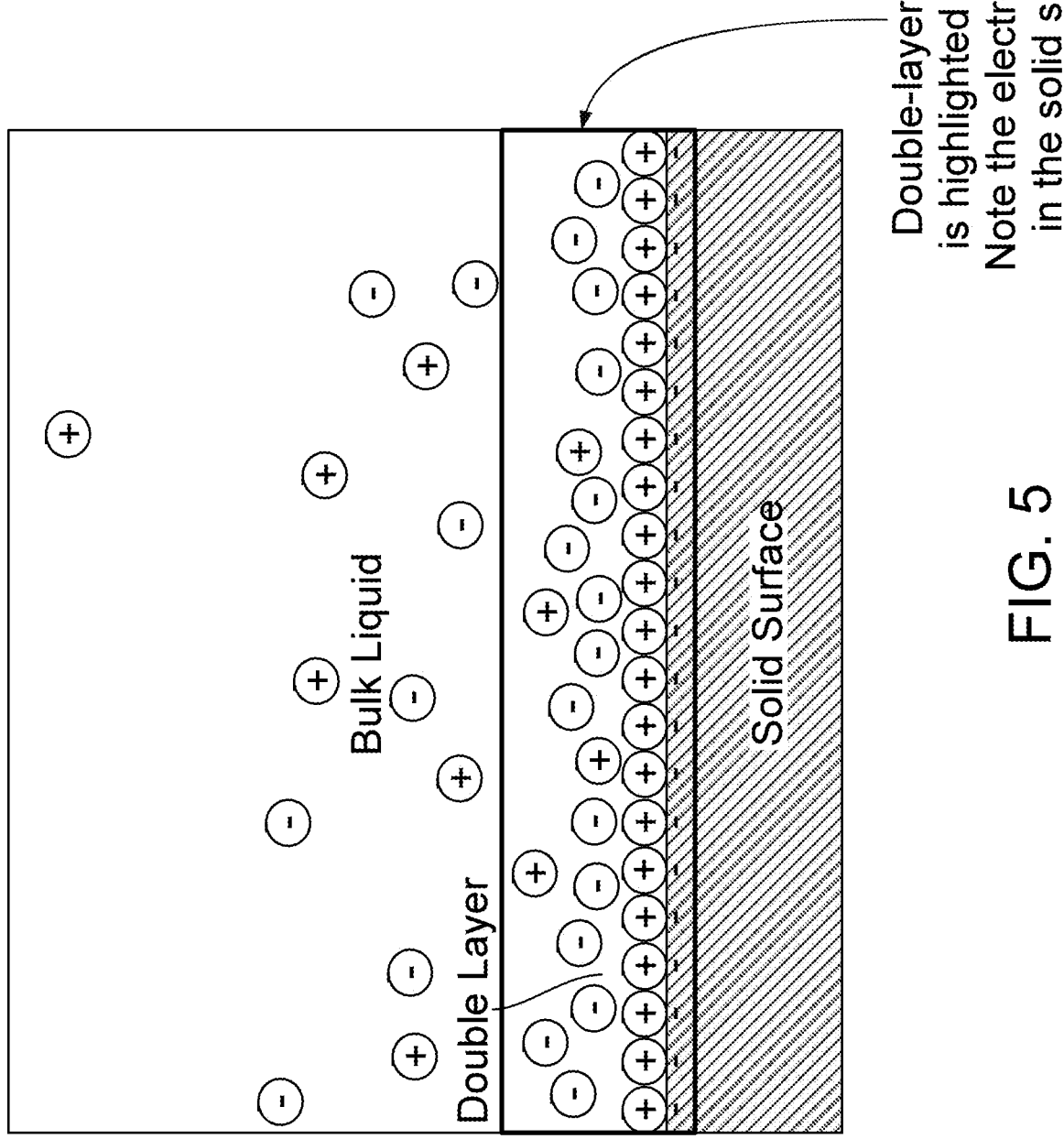
FIG. 5 illustrates a double layer that is formed at any interface between a conductive electrode and an adjacent liquid electrolyte.

FIG. 5 illustrates a double layer that is formed at an interface between a conductive electrode and an adjacent liquid electrolyte. An electrical model for the double layer is shown as electrical model 414 in FIG. 4 that models a capacitance associated with the working electrode. In the example shown, the electrode surface is negatively charged, resulting in the accumulation of positively charged species in the electrolyte. In another example, the polarity of all charges may be opposite to the example shown. The charge in the electrode is balanced by reorientation of dipoles and accumulation of ions of opposite charge in the electrolyte near the interface. The accumulation of charges on either side of the interface between electrode and electrolyte, separated by a small distance due to the finite size of charged species and solvent molecules in the electrolyte, acts like a dielectric in a conventional capacitor. The term "double layer" refers to the ensemble of electronic and ionic charge distribution in the vicinity of the interface between the electrode and electrolyte.

Figure 6:
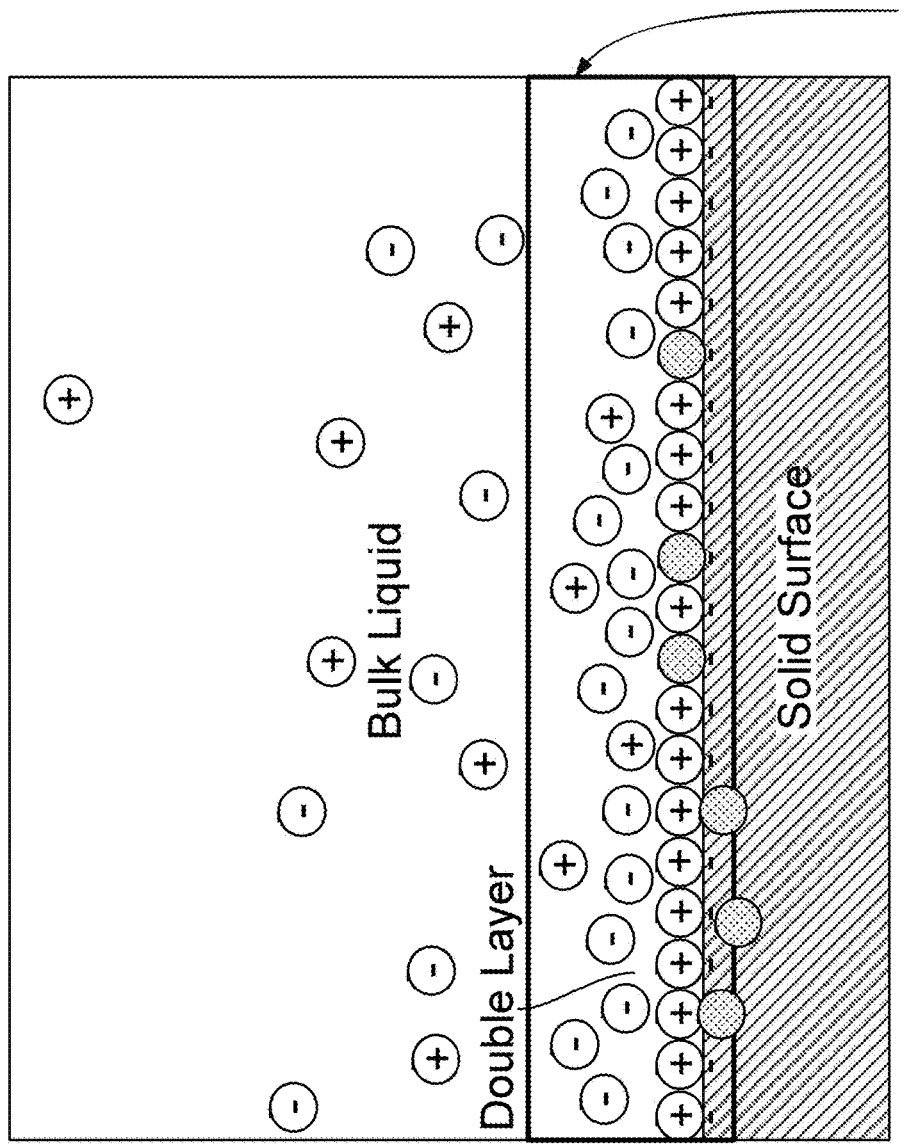
FIG. 6 illustrates a pseudocapacitance effect that can be formed, simultaneously with the formation of a double-layer, at an interface between a conductive electrode and an adjacent liquid electrolyte.

FIG. 6 illustrates a pseudocapacitance effect that can be formed, simultaneously with the formation of a double-layer as in FIG. 5, at an interface between a conductive electrode and an adjacent liquid electrolyte. FIG. 6 shows a double-layer with the addition of pseudo capacitance from charge transfer resulting in adsorption, intercalation, or reduction-oxidation reactions limited by available surface area (represented by solid circles).

E. Example Process of Constructing Porous Working Electrode

Figure 7:
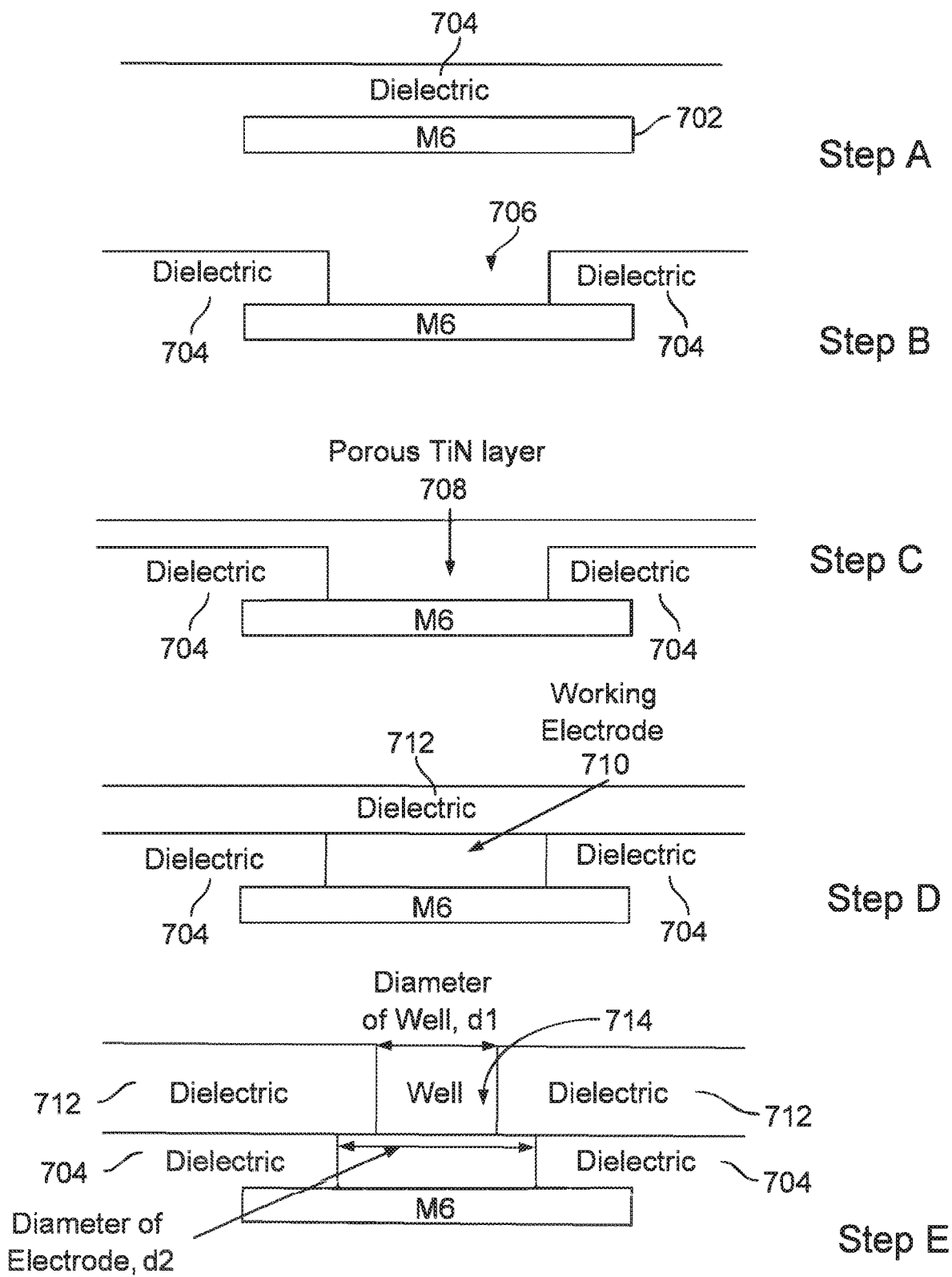
FIG. 7 illustrates an embodiment of a process for constructing an electrochemical cell of a nanopore-based sequencing chip that includes a TiN working electrode with increased electrochemical capacitance.

FIG. 7 illustrates an embodiment of a process for constructing an electrochemical cell of a nanopore-based sequencing chip that includes a TiN working electrode with increased electrochemical capacitance. The increased electrochemical capacitance can also be achieved with other electrodes having a porous structure and increased surface area.

At step A, a layer of dielectric 704 (e.g., $SiO_2$) is disposed on top of a conductive layer 702. The conductive layer can be part of circuitries that deliver the signals from the cell to the rest of the chip. For example, the circuitries deliver signals from the cell to an integrating capacitor, and conductive layer 702 can be a metal six (M6) layer of the underlying circuitry. In some embodiments, the layer of dielectric 704 has a thickness of about 400 nm.

At step B, the layer of dielectric 704 is etched to create a hole 706. The hole 706 provides a space for forming the spongy and porous TiN electrode.

At step C, a spongy and porous TiN layer 708 is deposited to fill the hole 706 created at step B. The spongy and porous TiN layer 708 is grown and deposited in a manner to create rough, sparsely-spaced TiN columnar structures or columns of TiN crystals that provide a high specific surface area that can come in contact with an electrolyte. The layer of spongy and porous TiN layer 708 can be deposited using different deposition techniques, including atomic layer deposition (ALD), chemical vapor deposition (CVD), physical vapor deposition (PVD) sputtering deposition, and the like. For example, layer 708 may be deposited by chemical vapor deposition using $TiCl_4$ in combination with nitrogen containing precursors (e.g., $NH_3$ or $N_2$). Layer 708 may also be deposited by chemical vapor deposition using $TiCl_4$ in combination with titanium and nitrogen containing precursors (e.g., tetrakis-(dimethylamido) titanium (TDMAT) or tetrakis-(diethylamido) titanium TDEAT). Layer 708 may also be deposited by PVD sputtering deposition. For example, titanium can be reactively sputtered in an $N_2$ environment or directly sputtered from a Ti target or directly sputtered from a TiN target. The conditions of each of the deposition methods may be tuned in such a way to deposit sparsely-spaced TiN columnar structures or columns of TiN crystals. For example, when layer 708 is deposited by DC (direct current) reactive magnetron sputtering from a titanium (Ti) target, the deposition system can be tuned to use a low temperature, low substrate bias voltage (the DC voltage between the silicon substrate and the Ti target), and high pressure (e.g., 25 mT) such that the TiN can be deposited more slowly and more gently to form columns of TiN crystals. In some embodiments, the depth of the deposited layer 708 is about 1.5 times the depth of hole 706. The depth of the deposited layer 708 is between 500 angstroms to 3 microns thick. The diameter or width of the deposited layer 708 is between 20 nm to 100 microns.

With continued reference to FIG. 7, at step D, the excess TiN layer is removed. For example, the excess TiN layer may be removed using chemical mechanical polishing (CMP) techniques. The remaining TiN deposited in the hole 706 forms a spongy and porous Ti working electrode 710. After working electrode 710 is formed, a layer of dielectric 712 (e.g., $SiO_2$) is deposited on top of the dielectric 704 and working electrode 710. In some embodiments, the depth of dielectric 712 is between 100 nm to 5 microns.

At step E, the layer of dielectric 712 is etched to create a well 714 exposing only a portion of the upper base surface area of the working electrode. For example, the well may be etched by reactive-ion etching (RIE). Because the base surface area of the opening of the well is independent from the base surface area of the working electrode, $C_{membrane}$ and $C_{electrochemical}$ in the cell may be fine-tuned to obtain the desired $C_{membrane}$ and $C_{electrochemical}$ ratio. In some embodiments, the diameter (d1) of well 714 is between 20 nm to 100 microns.

An electrochemical cell of a nanopore-based sequencing chip having a spongy TiN working electrode has many advantages. Depending on the thickness of the TiN electrode (e.g., 500 angstroms to 3 microns thick), the specific surface area of the spongy TiN working electrode and its electrochemical capacitance (e.g., 5 picofarads to 500 picofarads per square micron of base area) have a 10-1000 times improvement over that of a flat TiN working electrode with substantially identical dimensions (e.g., substantially identical thickness and base surface area). Since the spongy TiN working electrode allows electrolyte to diffuse through easily, the diameter/width of the spongy TiN working electrode may extend beyond the diameter/width of the well, such that the base surface area of the well and the working electrode can be optimized independently to provide the desired ratio between $C_{membrane}$ and $C_{electrochemical}$ or improved system performance. Other advantages of using TiN include its low cost and ease of patterning and etching compared to other electrode materials, such as platinum.

Figure 8A:
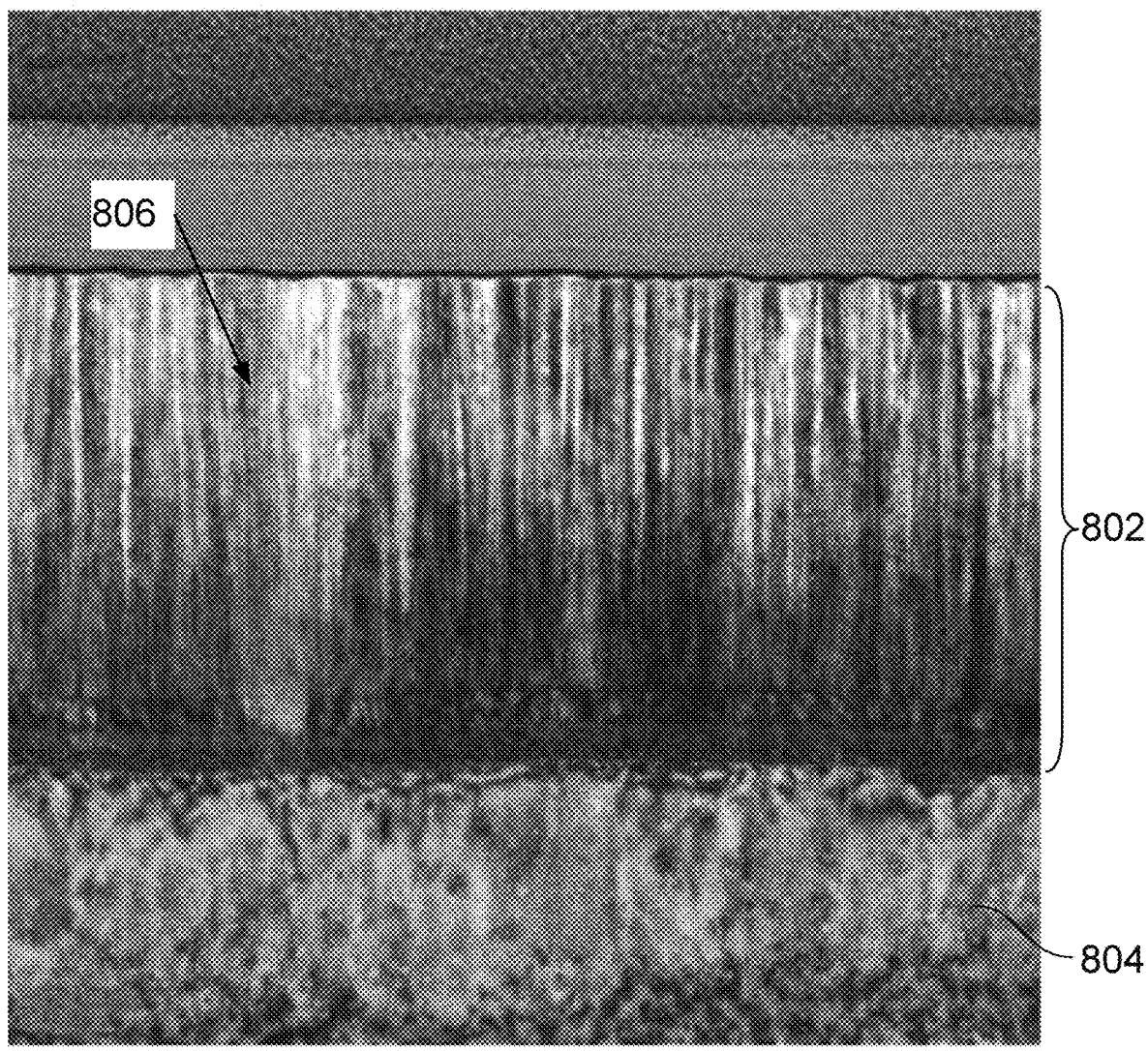
FIGS. 8A and 8B are micrographs illustrating a TiN electrode layer on a metal layer.
Figure 8B:
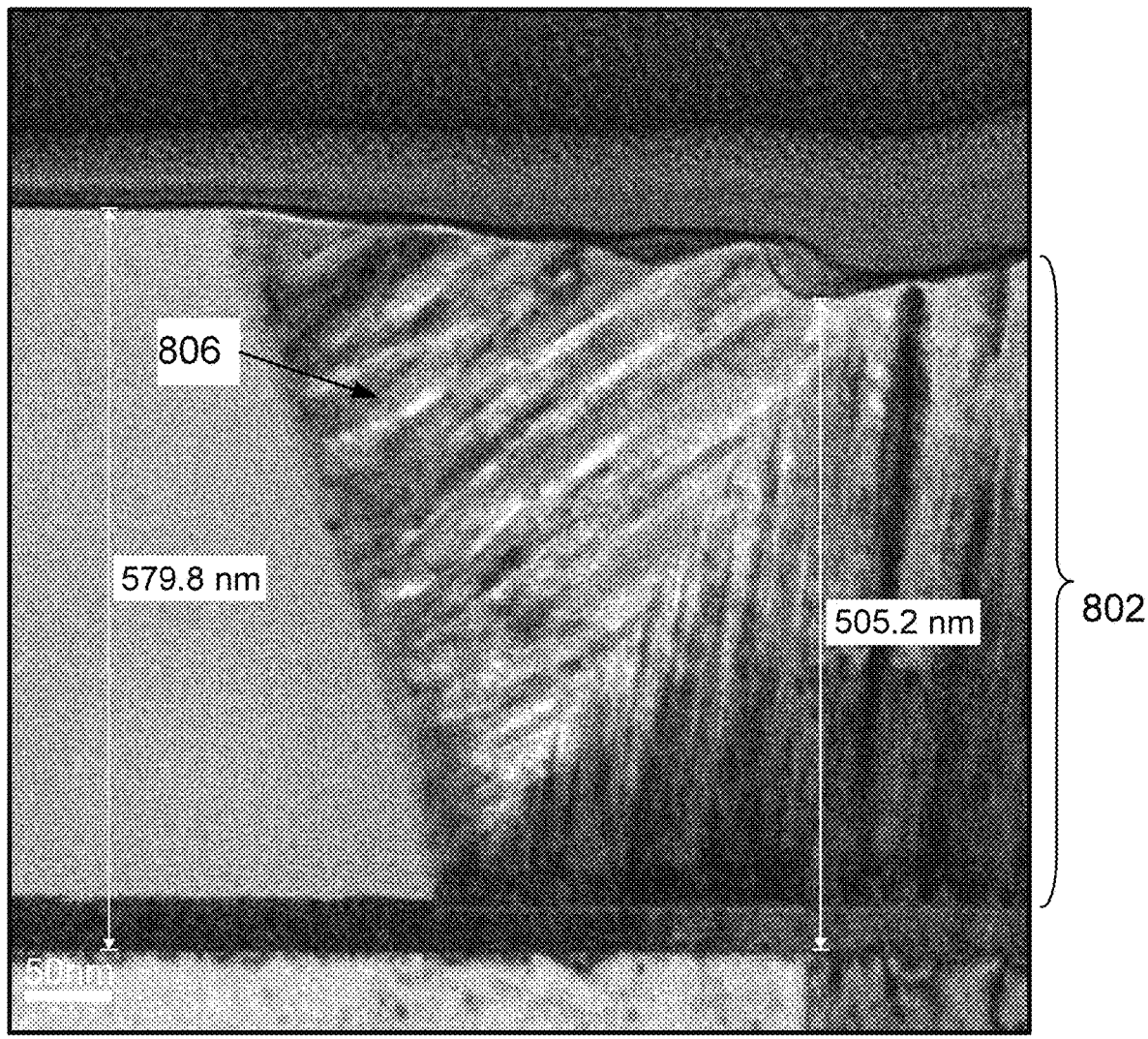

FIG. 8A is a micrograph illustrating a cross-section view of a spongy and porous TiN layer 802 deposited above a metal layer 804. As shown in FIG. 8A, the spongy and porous TiN layer 802 includes grass-like columnar structures 806. These structures can increase the surface area for the electrode, and thus the capacitance, which helps to reduce the effect of capacitance 416 from FIG. 4. FIG. 8B is another micrograph illustrating another cross-section view of a spongy and porous TiN layer 802 with TiN columnar structures 806 that are grown from the surface of the hole 706 at Step B of FIG. 7.

More details of the nanopore cells described above can be found in U.S. patent application Ser. No. 14/818,977, filed on Aug. 5, 2015, commonly owned and incorporated herein by reference in its entirety.

II. Shapes of Wells

Figure 9A:
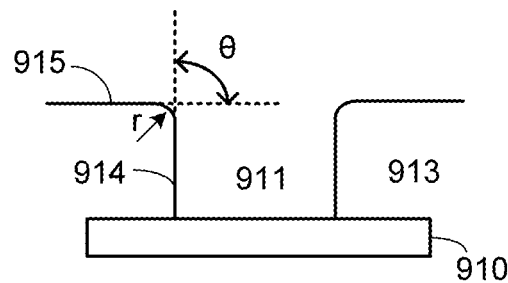
FIGS. 9A-9E illustrate microwell shapes according to various embodiments of the present invention.
Figure 9B:
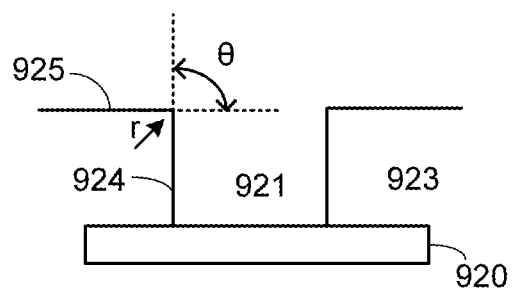
Figure 9C:
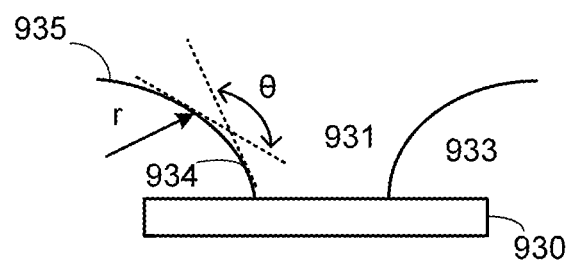
Figure 9D:
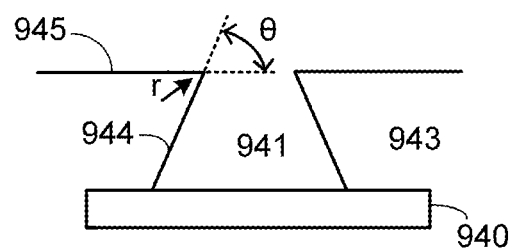
Figure 9E:
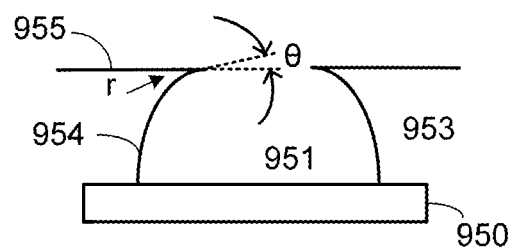

FIGS. 9A-9E are simplified cross-sectional views of various shapes of wells that can be used in a nanopore cell according to various embodiments of the invention. A nanopore cell has a well that has a well sidewall formed within a dielectric layer and a working electrode at the bottom of the well. The shape of the well can affect the formation of the nanopore device and its performance. FIG. 9A illustrates that the shape of the well can be described by a corner between a top surface of the dielectric layer and the well sidewall and the slope of the sidewall. FIGS. 9B and 9C illustrate wells with angles at well edge equal to or greater than 90°, and FIGS. 9D and 9E illustrate wells with angles at well edge less than 90° (reentrant profile). The well sidewall can be straight, slanted, or curved. The shape of the well may be affected by the material forming the well and the process condition. Possible effect of well shape on the well performance is also discussed.

A. Defining the Shape of a Well

FIG. 9A illustrates a well 911 overlying an electrode 910. Well 911 is surrounded by a dielectric material layer 913. Dielectric material layer 913 has a sidewall surface 914 and a top surface 915. The angle formed at the well edge between sidewall surface 914 and top surface 915 can be characterized as angle θ. The corner formed at the intersection of sidewall surface 914 and top surface 915 can be described by a radius of curvature r. In FIG. 9A, the angle θ is substantially 90°, and the corner at the well edge is rounded with a relatively small radius of curvature r.

The well profile (e.g., as defined by the angle and the sharpness of the well edge) can affect how fast the metastable bilayer structure forms and how robust it is. For electrical measurement, it is desirable to have a low capacitance of the bilayer (smaller time constant for voltage changes, thereby providing faster acquisition time) and a high double layer capacitance at the working electrode (decreases effect of double layer on the circuit by reducing impedance of the working electrode). The bilayer capacitance can be made smaller by reducing the size of the aperture or opening of the well, or making the bilayer membrane thicker. The double layer capacitance can be made larger by increasing the surface area of the working electrode. Further, the TiN electrode described above has a spongy and porous top surface that can increase the effective capacitance. Alternatively, a smaller bilayer capacitance and larger double layer capacitance can be achieved with a reentrant well profile, in which the well has a wider bottom base than the top opening.

The shape of the well can be influenced by the material and process used in forming the well. For example, a well can be formed in a layer of polyimide, which is a polymer of an imide monomers. A monomer is a functional group consisting of two acyl groups bound to nitrogen. Polyimide materials are known for thermal stability, good chemical resistance, excellent mechanical properties, and they are widely used in the electronics industry. A well formed by reactive ion etching (RIE) of polyimide tends to have a more vertical profile and sharp corners. In contrast, a well formed by photolithographic patterning of a polyimide layer tends to have more rounded corners and more sloped sidewalls. If a well is formed in an oxide layer, a wet etching process can undercut the oxide, leading to a wider bottom of the well. In addition, other materials can also be used to form a well with different profiles. For example, SU-8, which is an epoxy material, or CYTOP, which is a fluoropolymer, can also be used to form wells.

B. Angle at Well Edge Equal to or Greater than 90°

FIG. 9B illustrates a well 921 overlying electrode 920. Well 921 is surrounded by a dielectric material layer 923. Dielectric material layer 923 has a sidewall surface 924 and a top surface 925. The angle formed at the well edge between sidewall surface 924 and top surface 925 can be characterized as an angle θ of 90°. The corner formed at the intersection of sidewall surface 924 and top surface 925 can be described by a radius of curvature r. For example, the radius of curvature r can be as small as 10 Å. The well structure in FIG. 9B can be formed by, for example, RIE etching of a dielectric layer. The sharp corners can facilitate the formation of the bilayer membrane.

FIG. 9C illustrates a well 931 overlying electrode 930. Well 931 is surrounded by a dielectric material layer 933. Dielectric material layer 933 has a sidewall surface 934 and a top surface 935. The angle formed at the well edge between sidewall surface 934 and top surface 935 can be characterized as angle θ of greater by 90°. The corner formed at the intersection of sidewall surface 934 and top surface 935 can be described by a radius of curvature r of, e. g., 1-5 um. In FIG. 9C, well 931 has a wide rounded edge profile with a large angle θ and a large radius of curvature r. The well structure in FIG. 9C can be formed by photolithography patterning of a polyimide layer.

FIG. 9D illustrates a well 941 overlying electrode 940. Well 941 is surrounded by a dielectric material layer 943. Dielectric material layer 943 has a sidewall surface 944 and a top surface 945. In FIG. 9D, well 941 has a reentrant well edge profile, and the angle formed at the well edge between sidewall surface 944 and top surface 945 can be characterized as angle θ of less than 90°. The corner formed at the intersection of sidewall surface 944 and top surface 945 can be described by a small radius of curvature r. The sharp corners can facilitate the formation of the bilayer membrane. Further, the reentrant well profile can also provide a larger bottom area than the top aperture area. The well structure in FIG. 9D also provides a smaller bilayer membrane capacitance at the top aperture and a larger double layer capacitance at the working electrode. A method for forming the well structure of FIG. 9D is described in a section below.

FIG. 9E illustrates a well 951 overlying electrode 950. Well 951 is surrounded by a dielectric material layer 953. Dielectric material layer 953 has a sidewall surface 954 and a top surface 955. The angle formed at the well edge between sidewall surface 954 and top surface 955 can be characterized as angle θ. In FIG. 9E, well 951 has a reentrant well edge profile with an even smaller angle θ than the profile shown in FIG. 9D. The well sidewall has a concave profile forming a sharp angle θ with the top surface of the dielectric material. The corner formed at the intersection of sidewall surface 954 and top surface 955 can be described by a very small radius of curvature r. The sharp corners can facilitate the formation of the bilayer membrane. Similar to FIG. 9D, the reentrant profile of FIG. 9E also provides a smaller bilayer membrane capacitance at the top aperture and a larger double layer capacitance at the working electrode. This structure can be made by using a preexisting mandrel or by using a combination of RIE and wet etch.

III. Hydrophobicity Profiles

The surface properties of various parts of the well can affect the formation of the nanopore device and its performance. For example, it is desirable to have a working electrode that is wettable by aqueous solvents to facilitate the formation of the double layer. The wettability of a solid surface is determined by its surface energy and is often characterized by a water contact angle. Generally, if the water contact angle is less than 90°, the solid surface is considered hydrophilic, and if the water contact angle is greater than 90°, the solid surface is considered hydrophobic. Therefore, it is desirable that the working electrode is hydrophilic, which can be characterized by a water contact angle of less than 40°. In some cases, a surface can be considered hydrophilic if the water contact angle is less than 70°. In other cases, a surface can be considered hydrophilic if the water contact angle is less than 90°. It is desirable for the working electrode to be hydrophilic as this will increase the capacitance of the working electrode, thereby reducing its impedance effect on the circuit, which can cause voltage levels to move slightly as a result of charge build up after multiple measurements that involve switch 408 opening and closing.

The lipid that forms the membrane is in an organic solvent, and it is lipophilic. Lipophilic substances tend to dissolve in other lipophilic substances, while hydrophilic substances tend to dissolve in water and other hydrophilic substances.

The process of forming the bilayer over the aperture of the cell involves feeding reagents through the flow cell to set up the membrane. Factors that can influence the bilayer formation include the surface energy of all of the surfaces that are in contact with the liquid, the height of the flow cell, the flow rate of the liquids, and the viscosities of the fluids, etc. For example, it is desirable to have a hydrophobic surface around the aperture to wet with the organic solvent and lipid mixture that spans across the aperture.

The hydrophobicity of the well surface can be determined by the material and surface treatment used in the well construction. For example, the well can be formed in an oxide, and a silane treatment can change the oxide from hydrophilic to hydrophobic. Alternatively, the well can be formed in a polyimide layer, which is hydrophobic. The well can also be formed in CYTOP, which is a hydrophobic amorphous fluoropolymer. The sidewall surface and top surface of the well can have different arrangement of hydrophobicity.

Figure 10A:
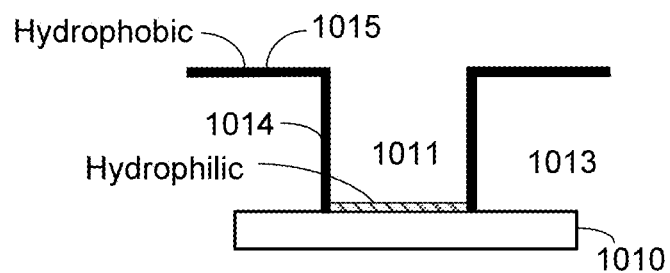
FIGS. 10A-10D illustrate microwell differential hydrophobicity according to various embodiments of the present invention.
Figure 10B:
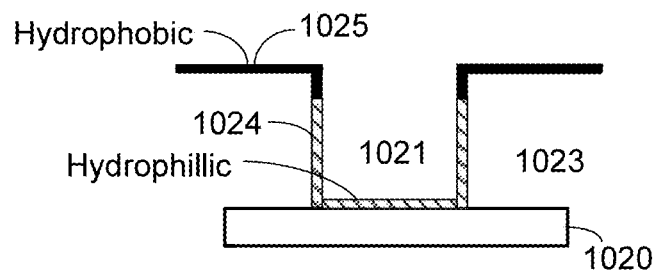
Figure 10C:
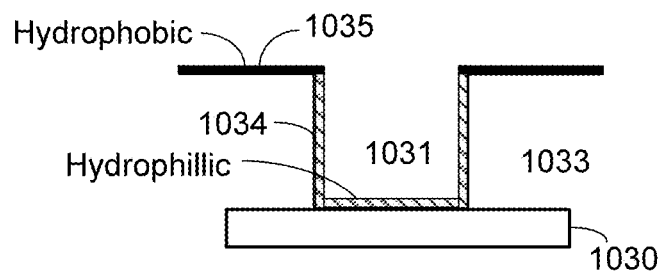
Figure 10D:
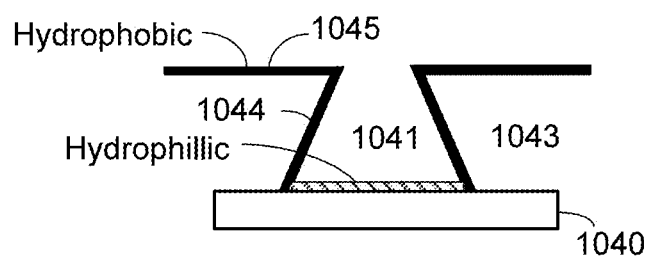

FIGS. 10A-10D are simplified cross-sectional views of various wells that have different surface properties. In FIGS. 10A-10C, a typical cell with vertical sidewalls and approximately 90° corners is used to illustrate the surface properties. However, the analysis of well surface properties can also be applied to other well profiles. For example, FIG. 10D illustrates a reentrant well having similar surface properties as the well in FIG. 10A.

A. Sidewalls are Hydrophobic

FIG. 10A illustrates a well 1011 overlying an electrode 1010. Well 1011 is surrounded by a dielectric layer 1013. Dielectric layer 1013 has a sidewall surface 1014 and a top surface 1015. In FIG. 10A, the top surface of electrode 1010 is hydrophilic, as illustrated with hatched marks. The well sidewall surface 1014 and top surface 1015 are hydrophobic, as illustrated by solid black lines. In this structure, the well can be made with a hydrophobic dielectric material (e.g., polyimide) over a hydrophilic electrode, for example, a TiN electrode. Alternatively, a well can be formed in an oxide layer, and then a silane treatment can be used to convert the oxide surface to become hydrophobic. As described above, the hydrophilic working electrode facilitates the wetting of the solvents in the well for forming contact with the solvents, and the hydrophobic top well surface is desirable for the formation of the bilayer membrane. As explained above in connection with FIG. 3, a membrane can be formed on top of dielectric layer 1013 and span across well 1011. For example, the membrane can include a lipid monolayer formed on top of hydrophobic top surface 1015. As the membrane reaches the opening of well 1013, the lipid monolayer can transition to a lipid bilayer that spans across the opening of the well. Having a hydrophobic surface (e.g., from a layer or a coating/film over a layer) can facilitate the formation of a lipid monolayer and the transition from a lipid monolayer to a lipid bilayer.

B. Sidewalls are Hydrophilic

FIG. 10B illustrates a well 1021 overlying an electrode 1020. Well 1021 is surrounded by a dielectric material layer 1023. Dielectric material layer 1023 has a sidewall surface 1024 and a top surface 1025. In FIG. 10B, the top surface of electrode 1020 is hydrophilic, as illustrated with hatched marks. An upper portion of the well sidewall surface 1024 and the well top surface 1025 are hydrophobic, as illustrated by solid black lines. However, a lower portion of the well sidewall surface 1024 is hydrophilic, as illustrated with hatched marks. Similar to the well structure in FIG. 10A, in FIG. 10B, the hydrophilic working electrode facilitates the wetting of the solvents in the well, and the hydrophobic top well surface is desirable for the formation of the bilayer membrane. This structure can be formed by using a hydrophilic liner in the well. It can also be created by using a film stack with a hydrophilic material closest to the electrode and a hydrophobic material on top. This could allow better wetting of the well (especially very small wells) and electrode.

FIG. 10C illustrates a well 1031 overlying an electrode 1030. Well 1031 is surrounded by a dielectric material layer 1033. Dielectric material layer 1033 has a sidewall surface 1034 and a top surface 1035. In FIG. 10C, the top surface of electrode 1030 is hydrophilic, as illustrated with hatched marks. The well top surface 1035 is hydrophobic, as illustrated by solid black lines. However, the well sidewall surface 1034 is hydrophilic, as illustrated with hatched marks. A method for forming the well structure of FIG. 10C can include depositing a layer of a hydrophilic dielectric material, coating the dielectric layer with a hydrophobic top surface layer, and then forming a well by an etching process. Similar to the well structure in FIG. 10A, the hydrophilic working electrode facilitates the wetting of the solvents in the well, and the hydrophobic top well surface is desirable for the formation of the bilayer membrane.

C. Reentrant Profile

FIG. 10D illustrates a reentrant well having similar surface properties as the well in FIG. 10A. FIG. 10D illustrates a reentrant well 1041 overlying an electrode 1040. Well 1041 is surrounded by a dielectric material layer 1043. Dielectric material layer 1043 has a sidewall surface 1044 and a top surface 1045. In FIG. 10A, the top surface of electrode 1040 is hydrophilic, as illustrated with hatched marks. The well sidewall surface 1044 and top surface 1055 are hydrophobic, as illustrated by solid black lines.

In this structure, the well can be made with a hydrophilic dielectric material such as polyimide over a hydrophilic electrode, such as a TiN electrode. An example method for forming a reentrant well using polyimide is described in a section below. Alternatively, a well can be formed in an oxide layer, and then a silane treatment can be used to convert the oxide surface to become hydrophobic. As described above, the hydrophilic working electrode facilitates the wetting of the solvents in the well, and the hydrophobic top well surface is desirable for the formation of the bilayer membrane. Further, the reentrant profile of FIG. 10D also provides a smaller bilayer membrane capacitance at the top aperture and a larger double layer capacitance at the working electrode.

IV. Protecting Working Electrode During Manufacturing

As described above, a nanopore well can be defined by a spongy and porous working electrode and a hydrophobic dielectric layer. Using a spongy and porous material for the working electrode (e.g., TiN) can provide increased surface area and higher double layer capacitance for the nanopore cells. However, if the hydrophobic dielectric layer (e.g., the polyimide layer or other hydrophobic layer) is formed directly on the porous electrode, residues of the hydrophobic dielectric material can be embedded in the gaps or cavities in the porous electrode, e.g., within the columnar structures of a TiN electrode. The organic residues can make the electrode surface less wettable and prevent fluid from contacting the surface of the electrode. As a result, the effective surface area can be reduced, causing a significant drop in the double layer capacitance at the electrolyte-electrode interface. To alleviate this problem, a thin buffer or sacrificial dielectric layer, such as an $SiO_2$ layer, can be formed on the electrode to protect the surface of the electrode prior to subsequent processing, such as the deposition of the polyimide layer. After the well is formed, the thin sacrificial dielectric layer can be removed from the top surface of the electrode. The thin buffer or sacrificial dielectric layer serves to protect the porous electrode layer from the hydrophobic layer during the well formation process.

A. Use of Dielectric Sacrificial Layer

1. Method of Manufacturing

FIGS. 11A-11F illustrate an embodiment of a process for constructing an electrochemical cell of a nanopore-based sequencing chip that includes a buffer for protecting a porous working electrode. After the formation of the working electrode, a buffer layer is formed on the working electrode, and then a hydrophobic dielectric layer is formed on the buffer layer. After the hydrophobic dielectric layer is etched to form the cavity of the well, the buffer layer is removed to expose the working electrode. During this process, the hydrophobic dielectric material does not form direct contact with the working electrode at the bottom of the well. The buffer layer can prevent organic residues from being embedded in the porous working electrode.

Figure 11A:
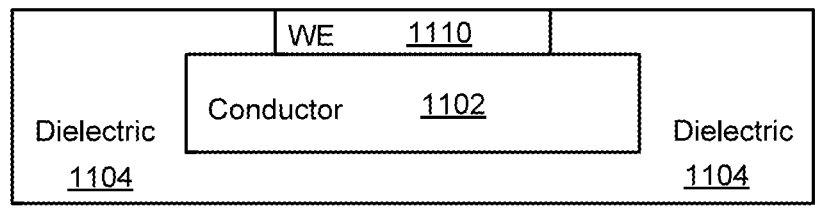
FIGS. 11A-11F illustrate an embodiment of a process for constructing an electrochemical cell of a nanopore-based sequencing chip that includes a dielectric layer for protecting a porous working electrode.

FIG. 11A shows a structure with a substrate having a conductive layer 1102 disposed in a top portion of the substrate and a dielectric layer 1104 surrounding conductive layer 1102, which can connect to a circuit, e.g., in a semiconductor layer. A porous electrode layer 1110 is formed on the conductive layer in an opening of the first dielectric layer 1104. The structure in FIG. 11A is similar to the structure shown in Step D in FIG. 7, and can be formed using the method described above in connection to FIG. 7.

Conductive layer 1102 can be part of circuitries that deliver the signals from the cell to the rest of the chip. In some cases, conductive layer 1102 can be the top metal layer of the circuitry, for example, the sixth metal layer labeled as M6 in FIG. 7. However, conductive layer 1102 is not limited to being the sixth metal layer of the underlying circuitry. Conductive layer 1102 can be, for example, an aluminum layer. As shown in FIG. 11A, conductive layer 1102 is enclosed in a layer of dielectric 1104 (e.g., $SiO_2$). Dielectric layer 1104 can include a dielectric layer formed on top of conductive layer 1102, which is already surrounded by a dielectric layer. In some embodiments, the layer of dielectric 1104 has a thickness of about 400 nm.

Next, the layer of dielectric 1104 is etched to create a hole, and a spongy and porous layer (e.g., TiN) is deposited to fill the hole. The spongy and porous layer can be grown in a manner to create rough, sparsely-spaced columnar structures or columns of crystals that provide a high specific surface area that can come in contact with an electrolyte. An example of the formation process for TiN is described above in connection with FIG. 7. In some embodiments, the depth of the deposited layer 1108 is about 1.5 times the depth of the hole. The depth of the deposited layer can be between 500 angstroms to 3 microns thick. The diameter or width of the deposited electrode layer can be between 20 nm to 100 microns. The excess electrode layer can be removed using chemical mechanical polishing (CMP) techniques. The remaining TiN deposited in the hole can form a spongy and porous working electrode (WE) 1110. In some cases, a titanium (Ti) adhesive layer can be formed between metal conductive layer 1102 and working electrode layer 1110.

Figure 11B:
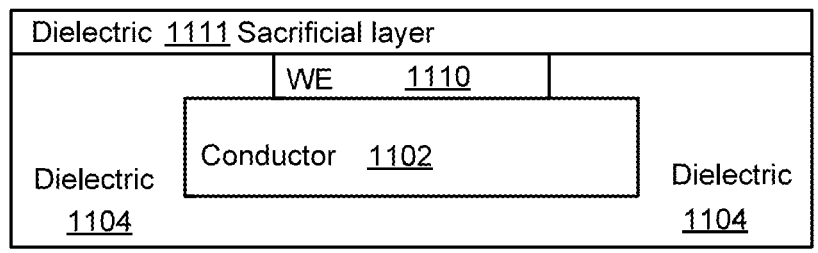

In FIG. 11B, a layer of dielectric 1111 (e.g., $SiO_2$) is deposited on top of the working electrode 1110 and the dielectric layer 1104. Dielectric layer 1111 is used as a buffer layer or sacrificial layer to protect the TiN electrode so it retains wettability and the increased double layer capacitance. This layer can be easily chemically removed without damaging the electrode and well materials. For example, this layer can be nonporous. Examples of a protective cap oxide are silicon oxide, titanium oxide, hafnium oxide, zirconium oxide. This material can be hydrophobic or hydrophilic. Dielectric layer 1111 can be a low temperature silicon oxide having a thickness of about 300 Å. The low temperature silicon oxide can be formed using a chemical vapor deposition (CVD) process at a temperature of, for example, 350° to 500°. Depending on the device requirement, the thickness of the $SiO_2$ layer 1111 can be between, for example, 100 Å to 1000 Å. Suitable dielectric materials for use in embodiments of the present invention (e.g., dielectric layer 1111) include, without limitation, oxides, nitrides (e.g., silicon mononitride or SiN), silicon oxide, silicon oxynitride, metal oxides, metal nitrides, metal silicates, transition-metal oxides, transition-metal nitrides, transition metal-silicates, oxynitrides of metals, metal aluminates, zirconium oxide, zirconium silicate, zirconium aluminate, hafnium oxide, titanium oxide, or combinations thereof Those of ordinary skill in the art will appreciate other dielectric materials that are suitable for use in the present invention.

Figure 11C:
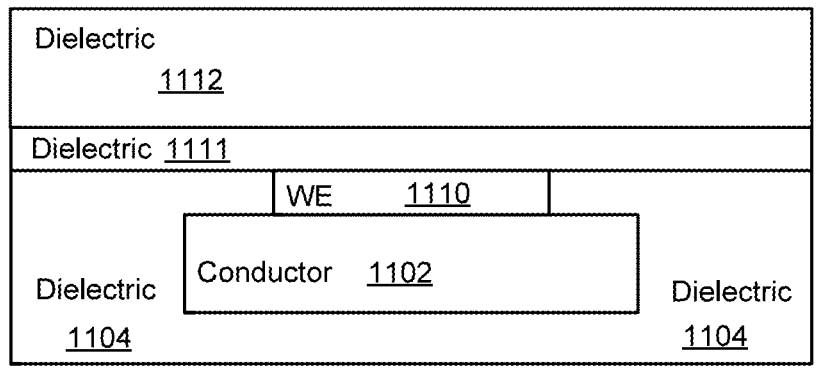

In FIG. 11C, a layer of dielectric layer 1112 (e.g., polyimide) is deposited on top of the dielectric layer 1111. For example, the polyimide layer can be formed by a spin-on process, which can be followed by a bake or curing process. The thickness of polyimide layer 1112 is selected according to the desired depth of the nanopore.

Figure 11D:
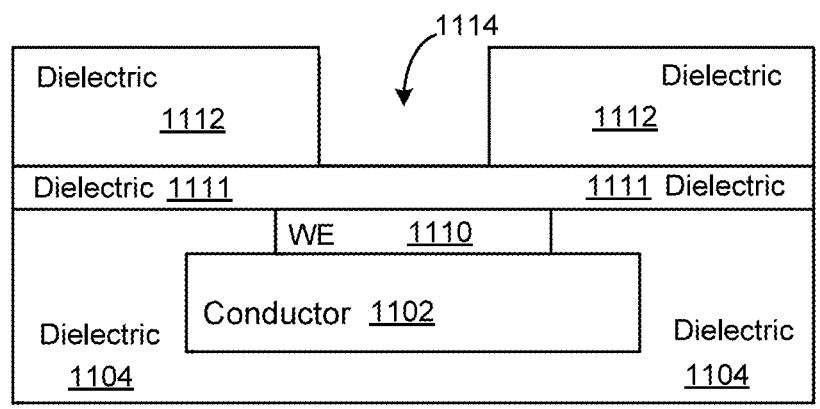

In FIG. 11D, the layer of dielectric 1112 is etched to create a cavity 1114 exposing a portion of the upper surface of dielectric layer 1111. As described above in connection with FIGS. 10A-10D, the polyimide layer can be patterned by reactive-ion etching (RIE) or by direct photolithographic patterning. In some embodiments, the depth of cavity 1114 can be between 20 nm to 100 microns. In this process, dielectric layer 1111 prevents polyimide layer 1112 from directly contacting electrode layer 1110. In some embodiments, the thickness of dielectric layer 1112 can be between 100 nm to 5 microns.

Figure 11E:
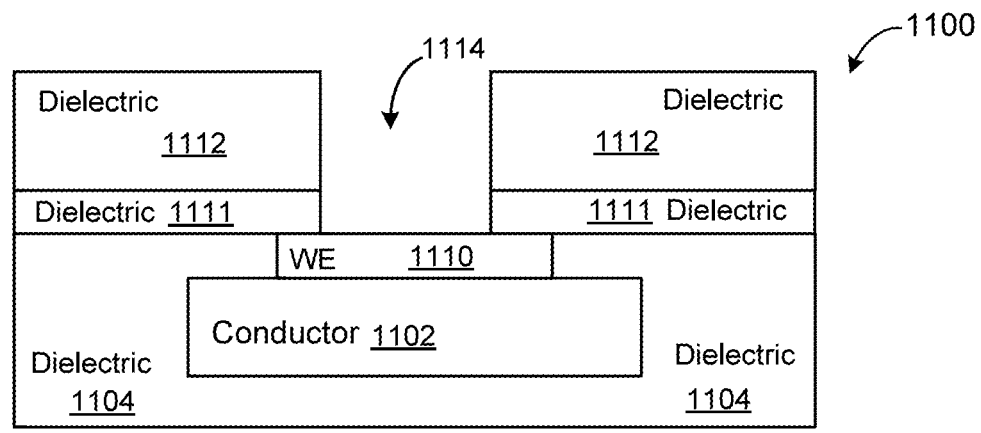

In FIG. 11E, the layer of dielectric 1111 is removed from cavity 1114 to expose a portion of the upper base surface area of the working electrode 1110 to form a well. For example, dielectric layer 1111 may be etched by a wet etching process using hydrofluoric acid (HF). Preferably, the etching process used to remove dielectric layer 1111 has proper selectivity such that it does not damage dielectric layer 1112 forming the sidewalls of the well and the top surface of the porous electrode that forms the bottom of the well. Further, the etching process does not leave etching residues or renders the top surface of the electrode to become hydrophobic, which may reduce the effective surface area of the electrode. In some embodiments, the diameter of cavity 1114 can be between 20 nm to 100 microns.

Figure 11F:
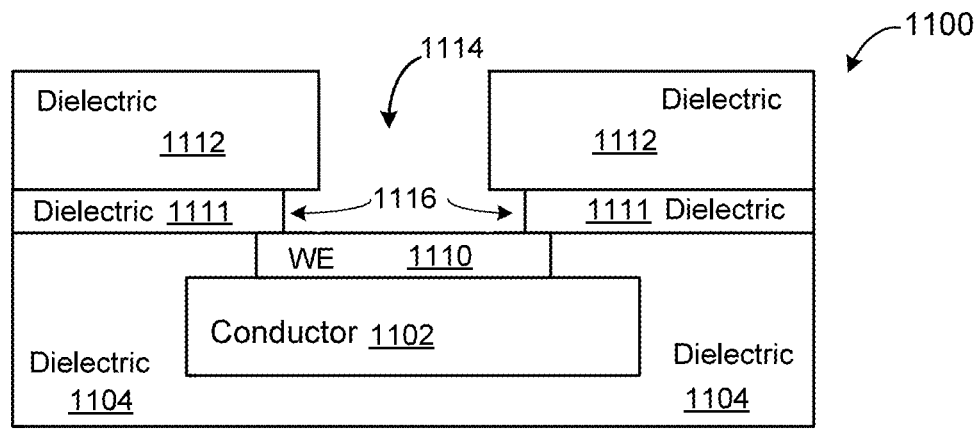

In FIG. 11F, undercut regions 1116 can be formed if a prolonged etching process is used to remove dielectric layer 1111.

2. Nanopore Device

FIG. 11F illustrates a nanopore cell 1100 that includes a conductive layer 1102 disposed in a top portion of a substrate, and a porous titanium nitride (TiN) electrode layer 1110 disposed on the conductive layer. As described above, the nanopore cell can be formed on top of a substrate, for example, a CMOS substrate, that includes circuitry for controlling the operation of the nanopore cell. Conductive layer 1102 can be a top metal layer of the underlying circuitry. For simplicity, the substrate is not shown in FIG. 11F. A first dielectric layer 1111, e.g., a silicon oxide layer, is disposed on the TiN electrode layer, and a polyimide layer 1112 is disposed on the first dielectric layer. A cavity or well 1114 is formed in the polyimide layer and the first dielectric layer 1111, the cavity exposing a portion of the TiN electrode layer. A well is formed by the cavity on the exposed portion of the TiN electrode layer. It can be seen in FIG. 11F that the well 1114 has a bottom base formed by the TiN electrode layer, and the well sidewall is formed by a polyimide layer over the first dielectric layer 1111.

Figure 12A:
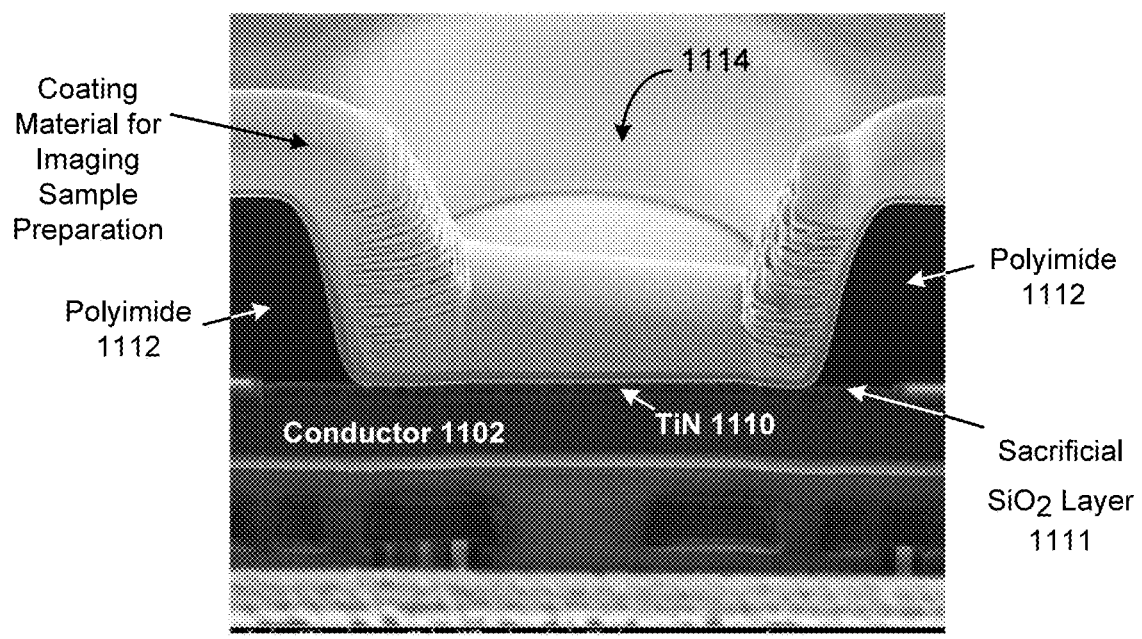
FIGS. 12A and 12B are SEM micrographs of an example of a nanopore device formed by the method of FIGS. 11A-11F.
Figure 12B:
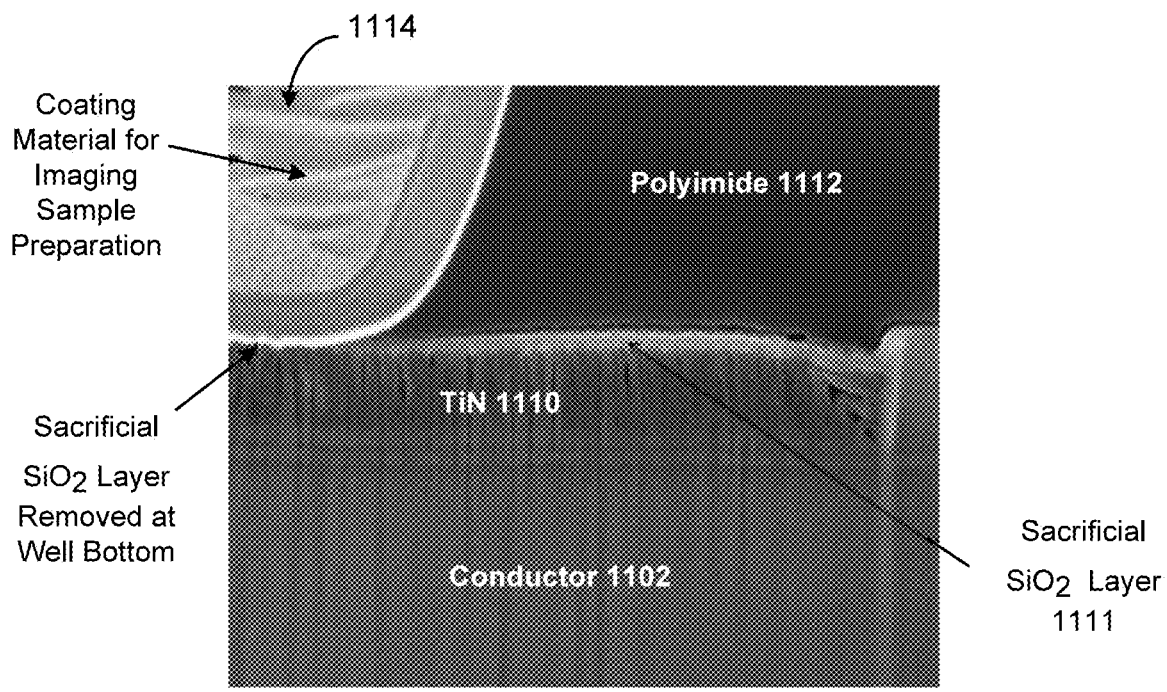

FIGS. 12A and 12B are SEM (scanning electron microscope) images illustrating an example of a nanopore device formed by the method of FIGS. 11A-11F. A well 1114 is formed in a cavity of a polyimide layer 1112. As shown in FIGS. 12A and 12B, well 1114 is filled with a coating material for SEM sample preparation. At the bottom of well 1114 is the top surface of TiN electrode 1110. The sidewalls of well 1114 are formed by a polyimide layer over a dielectric layer 1111, such as a silicon oxide layer. At the bottom of well 1114, the silicon oxide sacrificial layer is removed to expose the porous top surface of the TiN electrode for contact with the electrolyte in well 1114.

B. Protecting Working Electrode During Manufacturing Using a Metal Sacrificial Layer The embodiments described above are related to methods for protecting porous electrode material in order to preserve its high electric double-layer capacitance. The porous electrode material, if not protected, is susceptible to oxidation and polymer insertion which will result in a drastic reduction in double-layer capacitance. For example, an oxide film or other dielectric film can be deposited on the electrode surface as a protection layer, which will be removed when the chip is ready for usage.

In alternative embodiments, a metallic film, as opposed to an oxide film, can be used as the protective layer. Metallic films such as a titanium film can be deposited at low temperatures in a non-oxidizing, vacuum chamber to reduce exposure to an oxidizing ambient, which can reduce double-layer capacitance of porous electrode material. In addition, metal films such as titanium can be directly deposited in-situ following porous electrode material deposition in the same chamber without breaking vacuum. The metallic film is sacrificial and will be removed prior to chip when the chip is ready for usage.

1. Method of Manufacturing

FIGS. 13A-13G illustrate a process for constructing an electrochemical cell of a nanopore-based sequencing chip that includes a sacrificial metal layer for protecting a porous working electrode during cell manufacturing. In an embodiment, after the formation of the porous working electrode, a sacrificial metal layer is formed on the working electrode, and then a hydrophobic dielectric layer is formed on the sacrificial metal layer. After the hydrophobic dielectric layer is etched to form the cavity of the well, the sacrificial metal layer is removed to expose the working electrode. During this process, the hydrophobic dielectric material does not form direct contact with the working electrode at the bottom of the well. The sacrificial metal layer can prevent organic residues from being embedded in the porous working electrode. In the example illustrated in FIGS. 13A-13G, a titanium layer is used as the sacrificial metal layer. However, it is understood that other suitable metal or metal alloy layer can also be used.

Figure 13A:
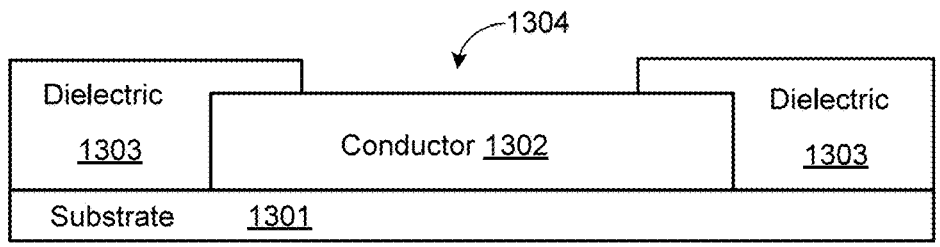
FIGS. 13A-13G illustrate a process for constructing an electrochemical cell of a nanopore-based sequencing chip that includes a sacrificial metal layer for protecting a porous working electrode during cell manufacturing.

FIG. 13A shows a device structure with a substrate 1301 having a conductive layer 1302 disposed in a top portion of the substrate and a dielectric layer 1303 surrounding conductive layer 1302, which can be connected to a circuit, e.g., in a semiconductor layer in the substrate. For example, conductive layer 1302 can be part of circuitries that deliver the signals from the cell to the rest of the chip. In some cases, conductive layer 1302 can be the top metal layer of the circuitry, for example, the sixth metal layer labeled as M6 in FIG. 7. However, conductive layer 1302 is not limited to being the sixth metal layer of the underlying circuitry. Conductive layer 1302 can be, for example, an aluminum layer. As shown in FIG. 13A, conductive layer 1302 is surrounded in a layer of dielectric 1303 (e.g., $SiO_2$). In some embodiments, the layer of dielectric 1303 has a thickness of about 400 nm. As shown in FIG. 13A, the layer of dielectric 1303 is etched to create an opening to expose a top surface of conductive layer 1302.

Figure 13B:
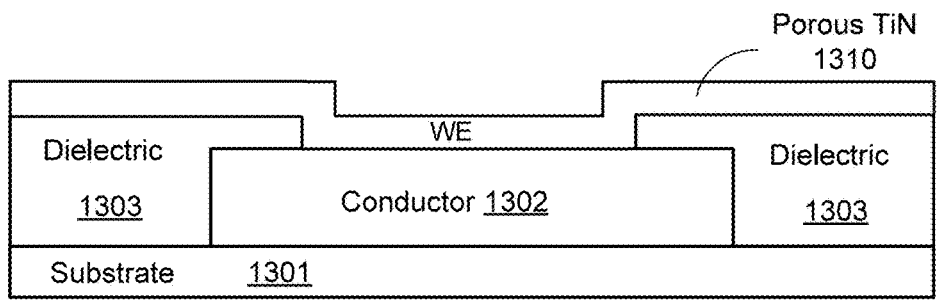

In FIG. 13B, a porous electrode layer 1310 is formed on the conductive layer 1302 in the opening of the first dielectric layer 1303 and on the first dielectric layer 1303. In some embodiments, the porous electrode 1310 can be a porous TiN layer formed using a process similar to the process described in connection to Step C of FIG. 7. The spongy and porous layer can be grown in a manner to create rough, sparsely-spaced columnar structures or columns of crystals that provide a high specific surface area that can come in contact with an electrolyte. The TiN deposited in the hole can form a spongy and porous working electrode (WE). In some cases, a titanium (Ti) adhesive layer can be formed between metal conductive layer 1302 and working electrode layer 1310.

Figure 13C:
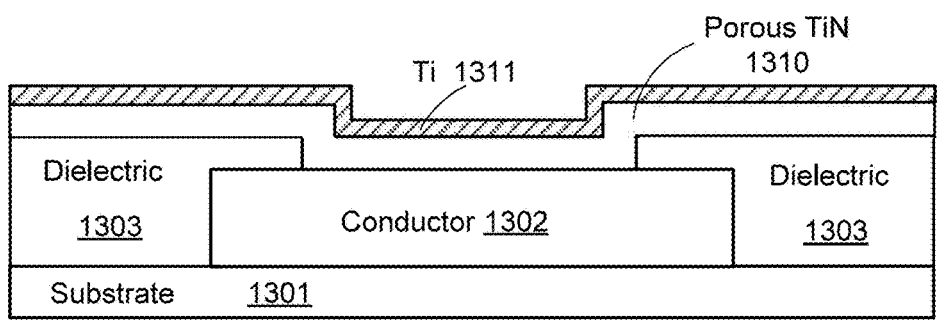

In FIG. 13C, a sacrificial metal layer or cap layer 1311 is deposited on top of the porous electrode layer 1310. In this example, the cap layer is a titanium (Ti) layer. The Ti layer 1311 can be deposited using different deposition techniques, including atomic layer deposition (ALD), chemical vapor deposition (CVD), physical vapor deposition (PVD) sputtering deposition, and the like. For example, Ti layer 1311 may be deposited by chemical vapor deposition using a precursor $TiCl_4$. Ti Layer 1311 may also be deposited by chemical vapor deposition using $TiCl_4$ in combination with titanium containing precursors (e.g., tetrakis-(dimethylamido) titanium (TDMAT) or tetrakis-(diethylamido) titanium TDEAT). Ti layer 1311 may also be deposited by PVD sputtering deposition. For example, titanium can be reactively sputtered in an inert environment or directly sputtered from a Ti target. In some embodiments, the porous TiN electrode layer 1310 and the Ti layer 1311 can be deposited in-situ in the same process chamber without breaking vacuum. In some embodiments, the thickness of the deposited Ti layer 1311 can be between 500 angstroms to 3 microns thick. For example, in a specific embodiment, the TiN layer 1310 is approximately 700 um thick and the Ti cap layer 1311 is approximately 300 um thick.

Figure 13D:
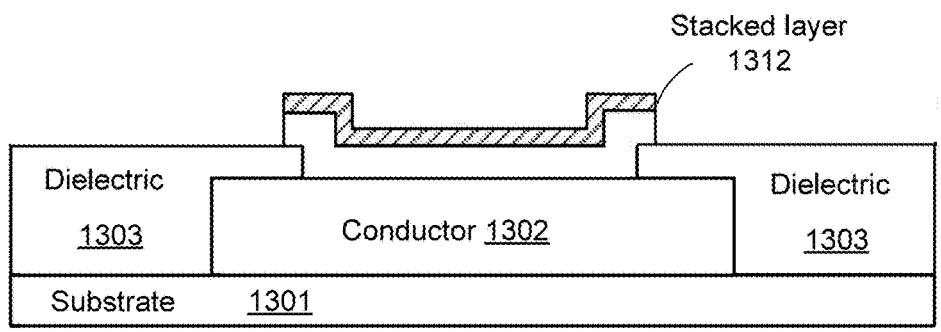
Figure 13E:
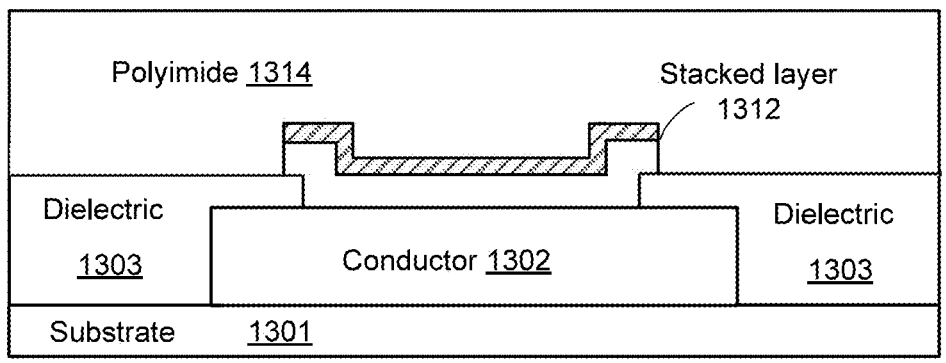

In FIG. 13D, the sacrificial metal layer Ti 1311 and the porous TiN electrode layer 1310 are patterned to form a patterned stacked layer 1312 covering the opening in the first dielectric layer. The stacked layer 1312 includes a portion of the porous TiN electrode layer 1310 and a portion of the sacrificial TiN layer 1311. The patterning of the sacrificial metal layer and the porous TiN electrode layer can be carried out using known lithography patterning process and etching process, such as a reactive ion etching (RIE) process In FIG. 13E, a dielectric layer 1314 is deposited on top of the Ti/TiN stacked layer 1312. Dielectric layer 1314 is used to form the walls of the nanopore cell. In this example, dielectric layer 1314 is a polyimide layer. For example, the polyimide layer can be formed by a spin-on process, which can be followed by a bake or curing process. The thickness of polyimide layer 1314 is selected according to the desired depth of the nanopore cell.

Figure 13F:
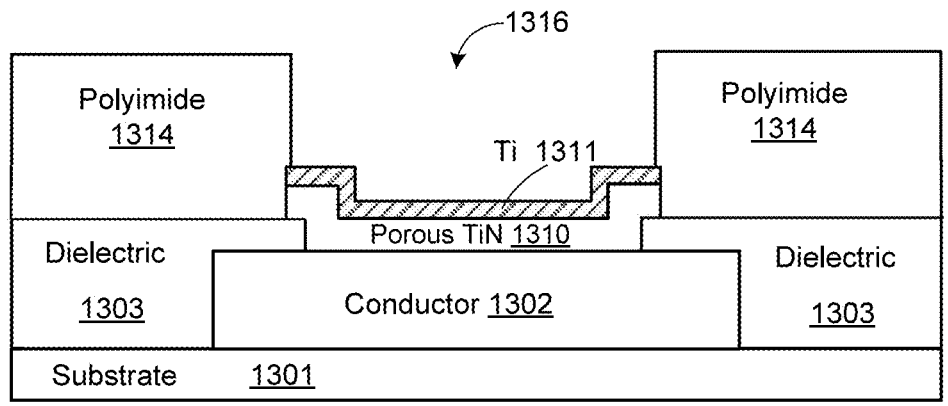

In FIG. 13F, a portion of the polyimide layer 1314 is etched to create a cavity 1316 to exposing a portion of the upper surface of Ti layer 1311. As described above in connection with FIGS. 10A-10D, the polyimide layer can be patterned by reactive-ion etching (RIE) or by direct photolithographic patterning. In some embodiments, the diameter of cavity 1316 can be between 20 nm to 100 microns. In this process, Ti layer 1311 prevents polyimide layer 1314 from directly contacting porous electrode layer 1310.

Figure 13G:
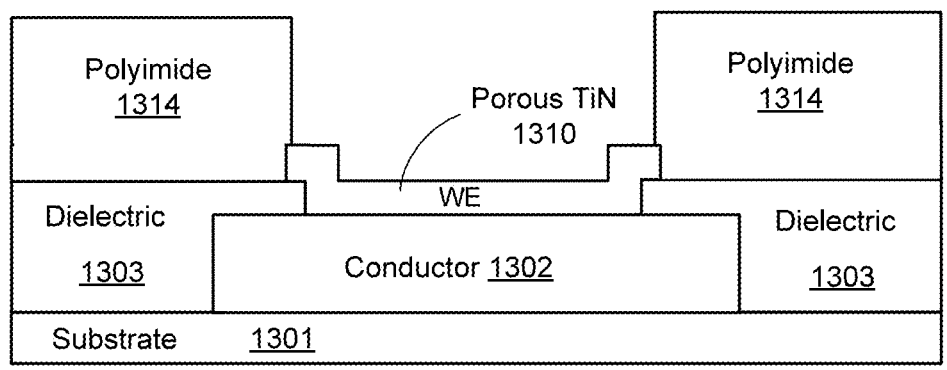

In FIG. 13G, the Ti layer 1311 is removed from cavity 1316 to expose a portion of the top surface area of porous TiN layer 1310 to form the lower base of the well. For example, the sacrificial Ti layer 1311 may be etched by a wet etching process using hydrofluoric acid (HF). Preferably, the etching process used to remove metal layer 1311 has proper selectivity such that it does not damage polyimide layer 1312 forming the sidewalls of the well and the top surface of the porous electrode that forms the bottom of the well. Further, the etching process should not leave etching residues or renders the top surface of the electrode to become hydrophobic, which may reduce the effective surface area of the electrode. After the removal of Ti layer 1311, porous TiN layer 1310 will function as the working electrode (WE) of the well.

2. Device Evaluation

Figure 14A:
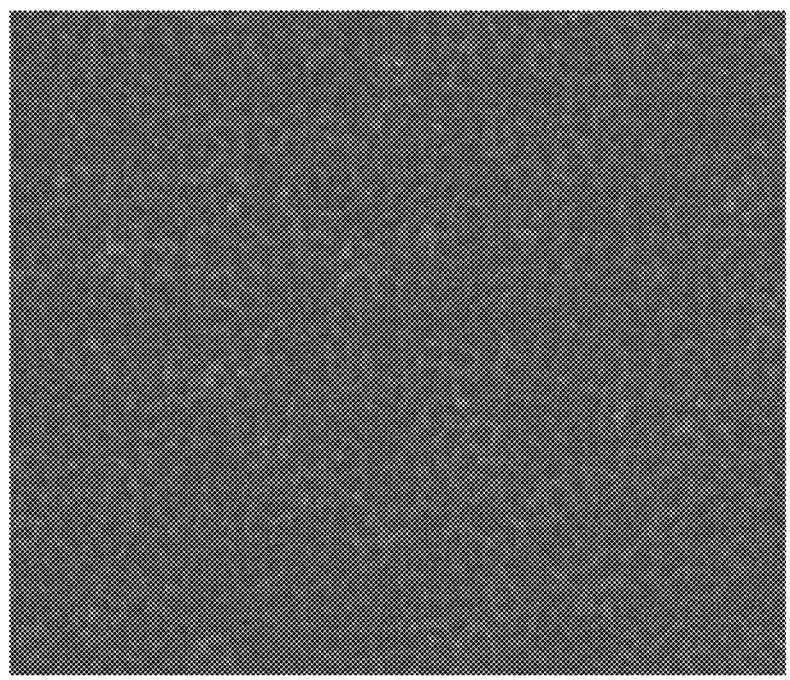
FIGS. 14A and 14B are SEM (scanning electron microscope) images illustrating an example of a device structure depicted in FIG. 13C.
Figure 14B:
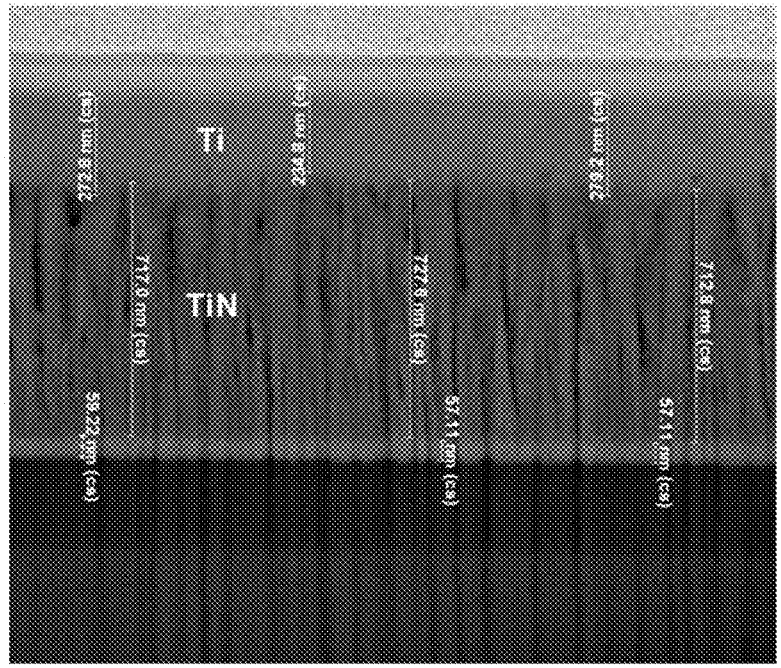

FIGS. 14A and 14B are SEM (scanning electron microscope) images illustrating an example of a device structure depicted in FIGS. 13A-13G. The device structure includes approximately 250 nm of titanium cap layer deposited on approximately 700 nm of porous TiN electrode layer. FIG. 14A is a top view of a surface of the deposited titanium layer. FIG. 14B is a cross-sectional view of a portion of the titanium cap layer deposited on the porous TiN electrode layer. It can be seen that the Ti layer only caps the surface of the porous TiN layer, and does not fill the gaps of the porous structures.

Figure 15:
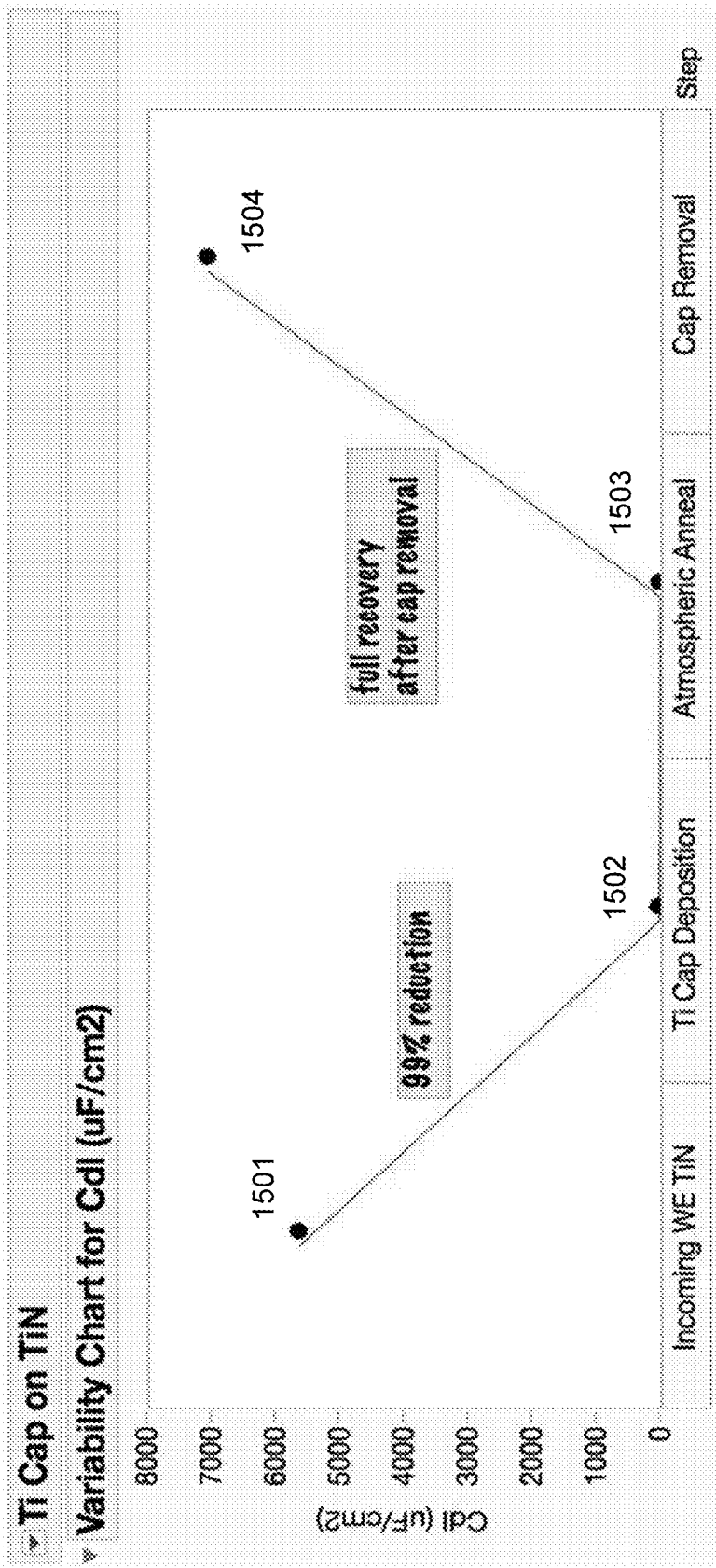
FIG. 15 is a diagram illustrating the double layer capacitance of a device structure including a sacrificial metal layer according to the method illustrated in FIGS. 13A-13G.

FIG. 15 is a diagram illustrating the double layer capacitance of a device structure having a sacrificial metal layer according to the method illustrated in FIGS. 13A-13G. The method includes approximately 250 nm of titanium sacrificial layer deposited on approximately 700 nm of porous TiN to protect the porous TiN electrode from the ambient and the polyimide layer. In FIG. 15, data point 1501 shows that the double-layer capacitance (Cdl) of the porous TiN electrode before the Ti cap deposition was about 5500 uF/cm^2. Data point 1502 shows that, after the Ti cap layer deposition, the double-layer capacitance dropped to about 30 uF/cm^2, signifying that the porous material had been sealed by the titanium layer. The substrate was then annealed at an elevated temperature in atmosphere to simulate environmental oxidation/contamination conditions. Data point 1503 shows that the double-layer capacitance substantially remain unchanged after the anneal process. The Ti cap layer was then removed with a hydrofluoric acid-based chemical. Data point 1504 shows the double-layer capacitance after the removal of the Ti cap. It can be seen that the double-layer capacitance of the porous electrode not only fully recovered its capacitance value, but also appeared to increase slightly. The increase in the double-layer capacitance may be due to the reducing effect or the oxygen gettering effect of the Ti protective layer. Alternatively, the increase in the double-layer capacitance may be due to prolonged exposure to the hydrofluoric acid-based chemical during the removal of the Ti cap layer. The data points in FIG. 15 demonstrate that the sacrificial Ti cap layer is effective in protecting the porous TiN electrode.

3. Alternative Processes

Figure 16A:
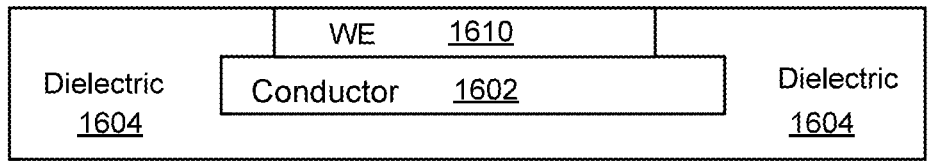
FIGS. 16A-16F illustrate a process for constructing an electrochemical cell of a nanopore-based sequencing chip that includes a reentrant well profile.

In some embodiments of the process described above in FIGS. 13A-13G, the Ti cap layer can be deposited in situ with the porous TiN electrode layer to protect the porous TiN electrode layer from exposure to the ambient. Alternatively, the Ti cap layer and the porous TiN electrode layer can be formed separately. Further, the Ti cap can be deposited after the porous TiN electrode is already deposited and patterned. For example, a process of forming the porous TiN electrode using a polishing (CMP) process is described in FIG. 7 and referenced in FIGS. 11A and 16A. Starting with a planarized porous TiN electrode as shown in FIG. 11A or 16A, a Ti cap layer can be deposited and then patterned before the deposition of the polyimide layer for forming the well.

In the above description, a titanium layer is used as an example of the sacrificial metallic cap layer. However, other metallic layers can also be used as the cap layer. The metal cap layer is used as a buffer layer or sacrificial layer to protect the porous TiN electrode so it retains wettability and high double layer capacitance. Therefore, it is desirable that the sacrificial protective layer be nonporous and can be removed without damaging the electrode and well materials. Examples of the protective metal cap material can include titanium, aluminum, tungsten, etc. The removal of the metal cap layer can be achieved using a wet chemical process including hydrofluoric acid, nitric acid, or combination of chemicals. The removal of the metal cap layer can also be achieved using reactive ion etch with reactive fluorine and oxygen species, etc. It is desirable that the etch process has adequate etch selectivity with respect to the porous TiN layer and the polyimide layer. Moreover, the process described in FIGS. 13A-13G, which does not include a polishing planarization step, can also be used with a dielectric sacrificial layer, such as a oxide layer.

V. Forming Reentrant Well Structure

As described above, a nanopore well having sharp corners with a reentrant profile and a hydrophobic top surface of the well can provide advantages in bilayer formation and improve cell performance, such as bilayer lifetime and stability. Therefore, a method for forming a reentrant well structure using a hydrophobic material is desirable. For example, the hydrophobic material can be a polyimide or a negative photolithographic material like SU-8. A method is described below using polyimide as an example. In some embodiments, a reentrant well structure is formed using a sacrificial dielectric structure that has a mandrel structure. The mandrel structure can be formed before a polyimide layer is formed around the sacrificial structure. The sacrificial structure has a wider bottom region than a top region. As a result, after the sacrificial structure is removed, the remaining polyimide layer has a cavity with a narrow opening and a wider base, forming a reentrant well. As an additional advantage, the dielectric sacrificial structure serves to protect the underlying electrode during the formation of the polyimide layer.

A. Method of Manufacturing

FIGS. 16A-16F illustrate a process for constructing an electrochemical cell of a nanopore-based sequencing chip that includes a reentrant well profile.

FIG. 16A shows a structure with a substrate having a conductive layer 1602 disposed in a top portion of the substrate and a dielectric layer 1604 surrounding conductive layer 1602. A porous electrode layer 1610 is formed on the conductive layer in an opening of the first dielectric layer 1604. The structure in FIG. 16A is similar to the structure shown in FIG. 11A, and can be formed using the method described above in connection to FIG. 16A.

In FIG. 16A, conductive layer 1602 can be part of circuitries that deliver the signals from the cell to the rest of the chip. In some cases, conductive layer 1602 can be the top metal layer of the circuitry, for example, the sixth metal layer labeled as M6 in FIG. 7. However, conductive layer 1602 is not limited to being the sixth metal layer of the underlying circuitry. Conductive layer 1602 can be, for example, an aluminum layer. As shown in FIG. 16A, conductive layer 1602 is enclosed in a layer of dielectric 1604 (e.g., $SiO_2$). Dielectric layer 1604 can include a dielectric layer formed on top of conductive layer 1602, which is already surrounded by a dielectric layer. In some embodiments, the layer of dielectric 1604 has a thickness of about 400 nm.

Next, the layer of dielectric 1604 is etched to create a hole, and an electrode layer (e.g., a spongy and porous TiN layer) is deposited to fill the hole. The spongy and porous layer is grown in a manner to create rough, sparsely-spaced TiN columnar structures or columns of TiN crystals that provide a high specific surface area that can come in contact with an electrolyte. An example of the TiN formation process is described above in connection with FIG. 7. In some embodiments, the depth of the deposited layer 1608 is about 1.5 times the depth of hole. The depth of the deposited electrode layer can be between 500 angstroms to 3 microns thick. The diameter or width of the deposited electrode layer can be between 20 nm to 100 microns. The excess electrode layer is removed using chemical mechanical polishing (CMP) techniques. The remaining electrode material deposited in the hole forms a spongy and porous electrode working electrode (WE) layer 1610. In some cases, an adhesive layer can be formed between metal layer and working electrode layer 1610. For example, for the TiN electrode layer, a titanium (Ti) adhesive layer can be formed between metal layer 1602 and TiN working electrode layer 1610.

Figure 16B:
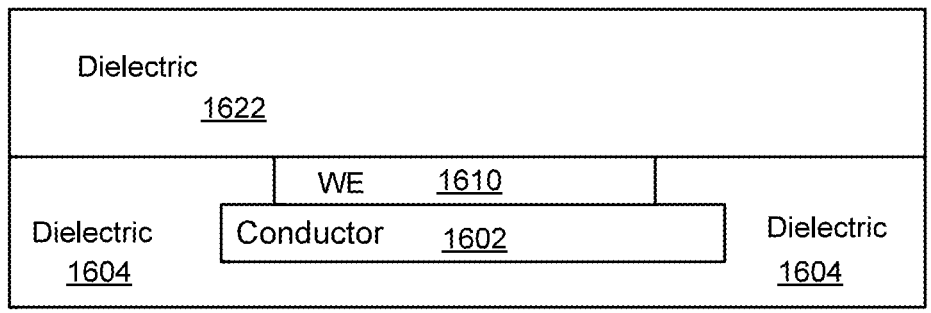

In FIG. 16B, a layer of dielectric 1622 (e.g., $SiO_2$) is deposited on top of the dielectric layer 1604 and working electrode 1610. The thickness of dielectric 1622 can be approximately 3 microns. In some cases, the thickness of dielectric layer 1622 can be, for example, between 100 nm to 5 microns.

Figure 16C:
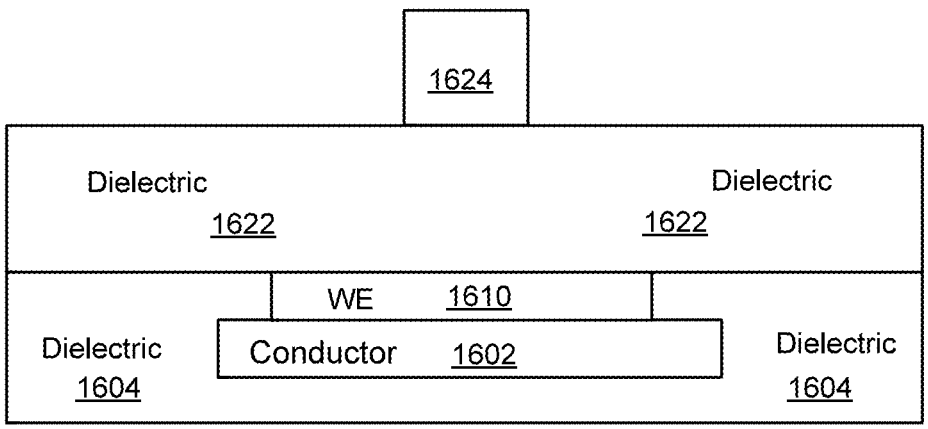
Figure 16D:
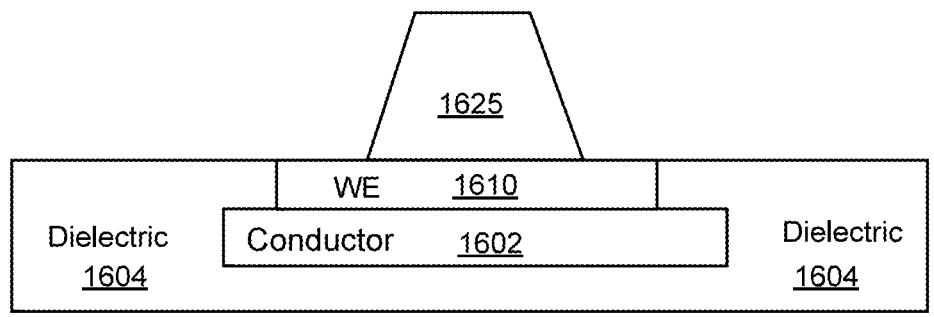

In FIG. 16C, a layer of photoresist is deposited on top of the dielectric 1622. The photoresist 1624 is then patterned to form an etch mask 1624. In FIG. 16D, dielectric layer 1622 is etched using etch mask 1624 to form a sacrificial or mandrel structure 1625 shown in FIG. 16D. In some embodiments, sacrificial or mandrel structure 1625 can have a circular or octagonal shape, and the diameter of sacrificial or mandrel structure 1625 can be between 20 nm to 100 microns. Different etch conditions can be used to change the angle of the remaining sacrificial or mandrel structure 1625. For example, the mandrel structure is smaller at the top and wider at the bottom.

Figure 16E:
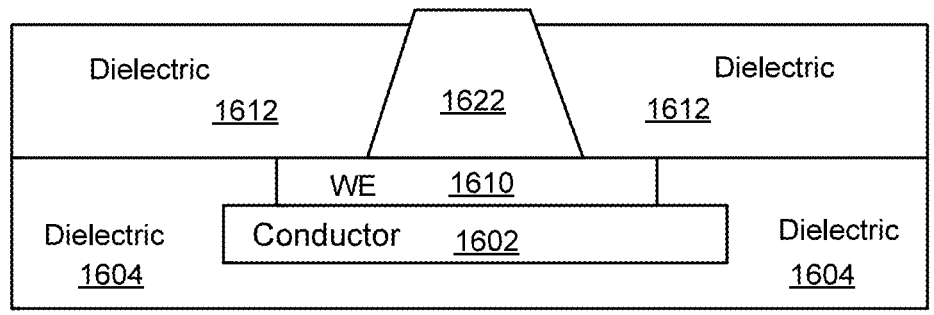

In FIG. 16E, the layer of dielectric 1612 (e.g., polyimide) is formed around sacrificial structure 1622. The sacrificial or mandrel structure remains on the working electrode layer 1610 during the formation of the polyimide layer to protect the electrode layer from directly contacting the polyimide layer. The polyimide layer 1612 can be formed by a spin-on process to a thickness just below the thickness of sacrificial structure 1622 to expose a top portion of sacrificial structure 1622. In some cases, the spun-on polyimide layer 1612 may be thicker than sacrificial structure 1622, and the polyimide layer 1612 can be etched back to expose a top portion of sacrificial structure 1622. The polyimide layer is then baked (partially or fully), which causes it to shrink in volume.

Figure 16F:
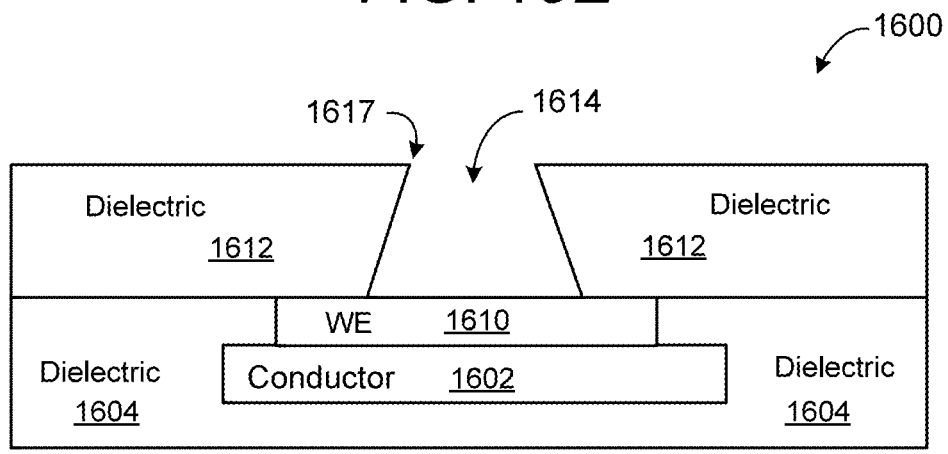

In FIG. 16F, sacrificial structure 1622 is removed by an etch process. For example, sacrificial structure 1622 made of silicon oxide can be etched away using a hydrofluoric acid (HF) wet etch process. The condition for the wet etch for removing the SiO2 structure 1622 is selected such that it does not damage the surface of the polyimide and does not have detrimental effects on the TiN working electrode surface. It can be seen that a well 1614 is formed in the cavity in the polyimide layer 1612. The well has reentrant sidewalls; the top edges of well 1614 have sharp angles 1617.

B. Nanopore Device

FIG. 16F illustrates a nanopore cell 1600 that includes a conductive layer 1602 disposed in a top portion of a substrate, a titanium nitride (TiN) electrode layer 1610 disposed on the conductive layer. As described above, the nanopore cell can be formed on top of a substrate, for example, a CMOS substrate, that includes circuitry for controlling the operation of the nanopore cell. Conductive layer 1602 can be a top metal layer of the underlying circuitry. For simplicity, the substrate is not shown in FIG. 16F. A polyimide layer 1612 is disposed on the TiN electrode layer 1610. A cavity or well 1614 is formed in the polyimide layer to expose a portion of the TiN electrode layer. A well having a reentrant profile is formed by the cavity on the exposed portion of the TiN electrode layer. It can be seen in FIG. 16E that the well 1614 has a wider bottom base formed by the TiN electrode layer and a narrower top opening with sharp corners 1617.

A nanopore well having sharp edges with a reentrant profile and hydrophobic top surface of the well may provide advantages in bilayer formation and improve cell performance. For example, the base surface area of the working electrode is greater than the base surface area of the opening of well. Therefore, the nanopore bilayer capacitance $C_{membrane}$ is smaller than the double layer capacitance $C_{electrochemical}$. The method described above for forming the well structure in FIG. 16F also provides the additional advantage that the dielectric sacrificial structure serves to protect the underlying TiN electrode during the formation of the polyimide layer.

VI. Forming Working Electrode Without a Polishing Process

In the methods described above, e.g., FIGS. 7, 11, 13, and 16, a polishing method may be used. For example, in FIG. 7, between Step C and Step D, a polishing method (e.g., CMP) may be used to remove the excess working electrode (TiN) material to form the working electrode 710 having a top surface that is substantially coplanar to the top surface of adjacent dielectric layers. In embodiments described below, the working electrode is formed without using a polishing method. This method can provide more working electrode surface area and better process control.

A. Method of Manufacturing

FIGS. 17A-17G illustrate a process for constructing an electrochemical cell of a nanopore-based sequencing chip without using a polishing method. The process also includes a sacrificial layer for protecting a porous working electrode during cell manufacturing. In an embodiment, after the formation of the porous working electrode, a sacrificial layer is formed on the working electrode. The sacrificial layer and the working electrode can be patterned using a lithographic process instead of a polishing process. Next, a hydrophobic dielectric layer is formed on the sacrificial layer. After the hydrophobic dielectric layer is etched to form the cavity of the well, the sacrificial layer is removed to expose the working electrode. During this process, the hydrophobic dielectric material does not form direct contact with the working electrode at the bottom of the well. The sacrificial layer can prevent organic residues from being embedded in the porous working electrode. In the example illustrated in FIGS. 17A-17G, a silicon oxide layer is used as the sacrificial metal layer. However, it is understood that other suitable dielectric materials, including silicon nitride, or combinations of dielectric materials, can also be used. Further, metals, such as those described above in connection with FIGS. 13A-13G, or metal alloy layers can also be used.

FIG. 17A shows a device structure with a substrate 1701 having a conductive layer 1702 disposed in a top portion of the substrate and a dielectric layer 1703 surrounding conductive layer 1702, which can be connected to a circuit, e.g., in a semiconductor layer in the substrate. For example, conductive layer 1702 can be part of circuitries that deliver the signals from the cell to the rest of the chip. In some cases, conductive layer 1702 can be the top metal layer of the circuitry, for example, the sixth metal layer labeled as M6 in FIG. 7. However, conductive layer 1702 is not limited to being the sixth metal layer of the underlying circuitry. Conductive layer 1702 can be, for example, an aluminum layer. As shown in FIG. 17A, conductive layer 1702 is surrounded in a layer of dielectric 1703 (e.g., $SiO_2$). In some embodiments, the layer of dielectric 1703 has a thickness of about 400 nm. As shown in FIG. 17A, the layer of dielectric 1703 is etched to create an opening to expose a top surface of conductive layer 1702.

In FIG. 17B, a porous electrode layer 1710 is formed on the conductive layer 1702 in the opening of the first dielectric layer 1703 and on the first dielectric layer 1703. In some embodiments, the porous electrode 1710 can be a porous TiN layer formed using a process similar to the process described in connection to Step C of FIG. 7. The spongy and porous layer can be grown in a manner to create rough, sparsely-spaced columnar structures or columns of crystals that provide a high specific surface area that can come in contact with an electrolyte. The TiN deposited in the hole can form a spongy and porous working electrode (WE). In some cases, a titanium (Ti) adhesive layer, also referred to as a seed layer, can be formed between metal conductive layer 1702 and working electrode layer 1710.

In FIG. 17C, a sacrificial layer, also referred to as a cap layer, 1711 is deposited on top of the porous electrode layer 1710. Cap layer 1711 is used as a buffer layer or sacrificial layer to protect the TiN electrode so it retains wettability and the increased double layer capacitance. This layer can be easily chemically removed without damaging the electrode and well materials. As an example, the cap layer can be an oxide layer. Examples of a protective cap oxide are silicon oxide (SiO2), titanium oxide, hafnium oxide, zirconium oxide, etc. This material can be hydrophobic or hydrophilic. Dielectric layer 1711 can be a low temperature silicon oxide having a thickness of about 300 Å. The low temperature silicon oxide can be formed using a chemical vapor deposition (CVD) process at a temperature of, for example, 350° to 500°. Depending on the device requirement, the thickness of the $SiO_2$ layer 1711 can be between, for example, 100 Å to 1000 Å. Suitable dielectric materials for use in embodiments of the present invention (e.g., dielectric layer 1711) include, without limitation, oxides, nitrides (e.g., silicon mononitride or SiN), silicon oxide, silicon oxynitride, metal oxides, metal nitrides, metal silicates, transition-metal oxides, transition-metal nitrides, transition metal-silicates, oxynitrides of metals, metal aluminates, zirconium oxide, zirconium silicate, zirconium aluminate, hafnium oxide, titanium oxide, or combinations thereof. Those of ordinary skill in the art will appreciate other dielectric materials that are suitable for use in the present invention.

In FIG. 17D, a photoresist layer 1712 is formed on the sacrificial layer 1711 and the porous TiN electrode layer 1710 and then patterned using a known lithography patterning process. The patterned photoresist layer 1712 is used as an etch mask in FIG. 17E.

In FIG. 17E, using the patterned photoresist layer 1712 of FIG. 17D as a mask, the sacrificial layer 711 and the porous TiN electrode layer 1710 are etched to form a patterned stacked layer 1713 covering the opening in the first dielectric layer. The stacked layer 1713 includes a portion of the porous TiN electrode layer 1710 and a portion of the sacrificial layer 1711. The stacked layer 1713 extends from the opening in the dielectric layer 1703 to cover a portion of the dielectric layer 1703, forming an overhang region 1717 in the TiN electrode layer 1710. The etch can be carried out using a known process, such as a reactive ion etching (RIE) process. After the etching, the photoresist mask is removed.

Figure 17F:
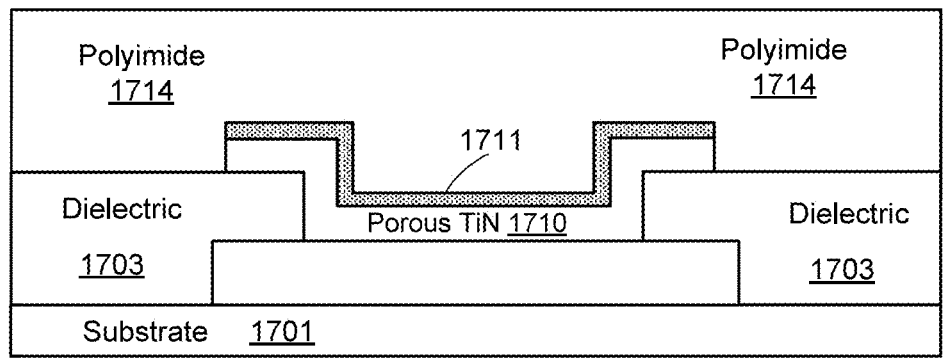

In FIG. 17F, a dielectric layer 1714 is deposited on top of the Ti/TiN stacked layer 1712. Dielectric layer 1714 is used to form the walls of the nanopore cell. In this example, dielectric layer 1714 is a polyimide layer. For example, the polyimide layer can be formed by a spin-on process, which can be followed by a bake or curing process. The thickness of polyimide layer 1714 is selected according to the desired depth of the nanopore cell.

Figure 17G:
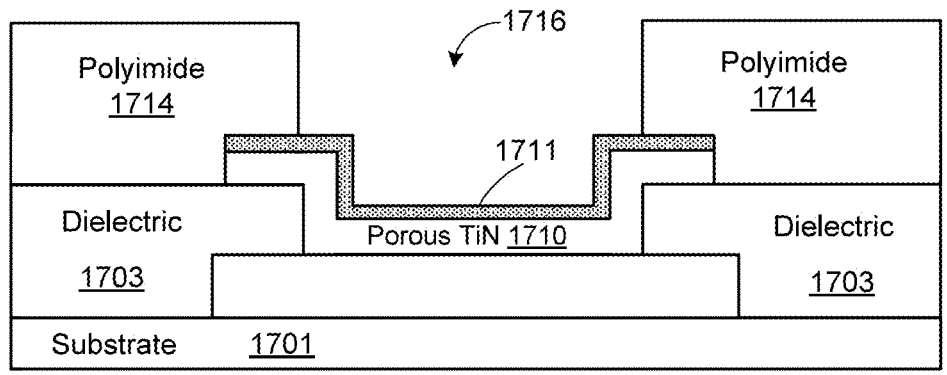

In FIG. 17G, a portion of the polyimide layer 1714 is etched to create a cavity 1716 to expose a portion of the upper surface of Ti layer 1711. As described above in connection with FIGS. 10A-10D, the polyimide layer can be patterned by reactive-ion etching (RIE) or by direct photolithographic patterning. In some embodiments, the diameter of cavity 1716 can be between 20 nm to 100 microns. In this process, the cap layer, or sacrificial layer, 1711 can prevent polyimide layer 1714 from directly contacting porous electrode layer 1710.

Figure 17H:
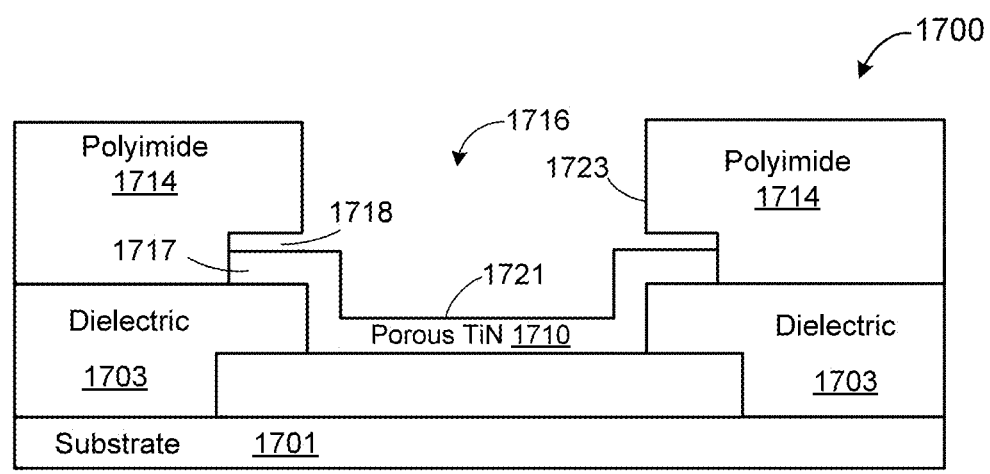

In FIG. 17H, the cap layer 1711 is removed from cavity 1716 to expose a portion of the top surface area of porous TiN layer 1710 to form the lower base of the well. For example, the sacrificial layer 1711 may be etched by a wet etching process using hydrofluoric acid (HF). Preferably, the etching process used to remove sacrificial layer 1711 has proper selectivity such that it does not damage polyimide layer 1712 forming the sidewalls of the well and the top surface of the porous electrode that forms the bottom of the well. Further, the etching process should not leave etching residues or renders the top surface of the electrode to become hydrophobic, which may reduce the effective surface area of the electrode. After the removal of Ti layer 1711, porous TiN layer 1710 will function as the working electrode (WE) of the well.

B. Nanopore Device

FIG. 17H illustrates a nanopore cell 1700 that includes a substrate 1701, a conductive layer 1702 disposed in a top portion of the substrate 1701, and a first dielectric layer 1703 overlying the conductive layer 1702. The first dielectric layer has an opening exposing a portion of the conductive layer, as shown in FIG. 17A. An electrode layer 1710 is disposed in the opening of the first dielectric layer 1703. The electrode layer has an overhang portion 1717 extending over the first dielectric layer 1703 to overlap a portion of the first dielectric layer 1703. A second dielectric layer 1714 is disposed on the first dielectric layer 1703. A cavity 1716 in the second dielectric layer 1714 exposes a portion of the electrode layer 1710. The cavity including an undercut portion 1718 of the second dielectric layer 1714 above the overhang portion 1717 of the electrode. Nanopore cell 1700 includes a well formed by the cavity 1716, which has a bottom base 1721 formed by a top surface of the electrode layer 1710 and well sidewalls 1723 formed by the second dielectric layer 1714.

In the example of FIG. 17H, the electrode layer 1710 includes porous TiN (titanium nitride), the first dielectric layer 1703 includes an oxide layer, and the second dielectric layer 1714 includes polyimide. Other suitable material can also be used, as described above in connection to FIGS. 7, 13A-13E, 16A-16F, and 17A-17H. For example, the second dielectric layer 1714 can include an organic material.

In some embodiments of the nanopore cell of FIG. 17H, the overhang portion can have a length in a range of 0.3 μm to 5 μm, the undercut portion can have a length in a range of 0.2 μm to 5 μm, the well can have a width in a range of 1 μm to 10 μm and a depth in a range of 1 μm to 4 μm.

Nanopore device 1700 can provide many advantages. For example, the exposed surface area of the electrode 1710 can be increased as a result of the overhang portion 1717 of the electrode 1710 and the undercut portion 1718 under the second dielectric layer 1714, thereby increasing the double layer capacitance $C_{electrochemical}$. Further, the surface of the vertical portion of the electrode can also contribute to the overall surface area of the electrode. As a result, the base surface dimension of the working electrode can be greater than the base surface area of the well opening. Therefore, the nanopore double layer capacitance $C_{electrochemical}$ can be larger than the bilayer capacitance $C_{membrane}$, which can improve cell performance, as described above. Moreover, the overhang portion 1717 of the electrode 1710 overlaps the edges of the first dielectric layer 1703, which can provide process margin and improve process control.

VII. Surface Treatment for Increased Double Layer Capacitance

Some embodiments can increase the porosity of the porous electrode, thereby increasing the effective area for increased double layer capacitance. In some of the examples described above, a protective thin film is deposited on the porous electrode to shield it from the organic film, such as polyimide, which forms the well boundaries. The protective film, or sacrificial film, can be removed with a chemistry (mixture) containing high concentration of hydrofluoric acid (HF). The protective film removal chemistry can be extended to increase the electrode double-layer capacitance by etching the electrode and making it more porous in the process. However, high concentration HF can be non-selective towards the underlying device's passivation dielectrics, and, therefore, poses risks of short circuits if applied over extended periods of time. An improved surface treatment method is described below.

A. Method of Surface Treatment

Figure 18A:
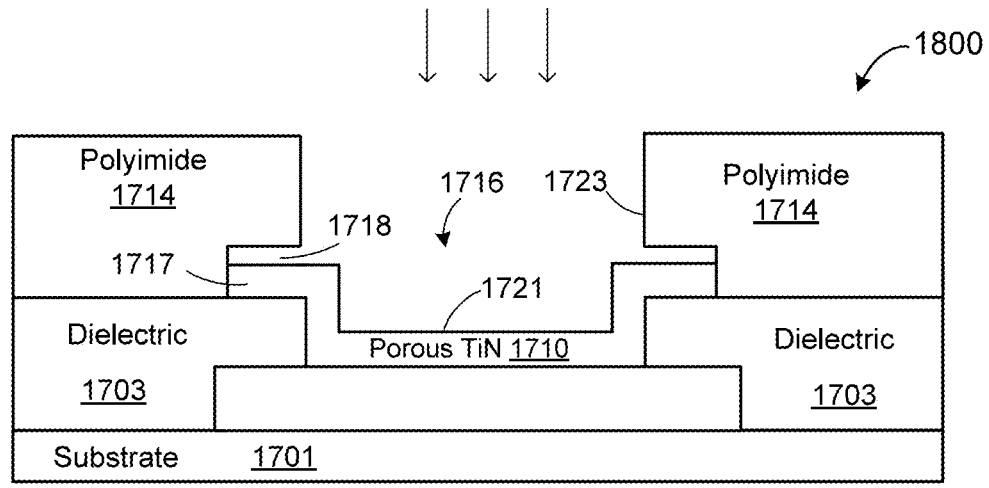
FIGS. 18A and 18B are cross-sectional views of representative nanopore device structures that are suitable for the surface treatment.
Figure 18B:
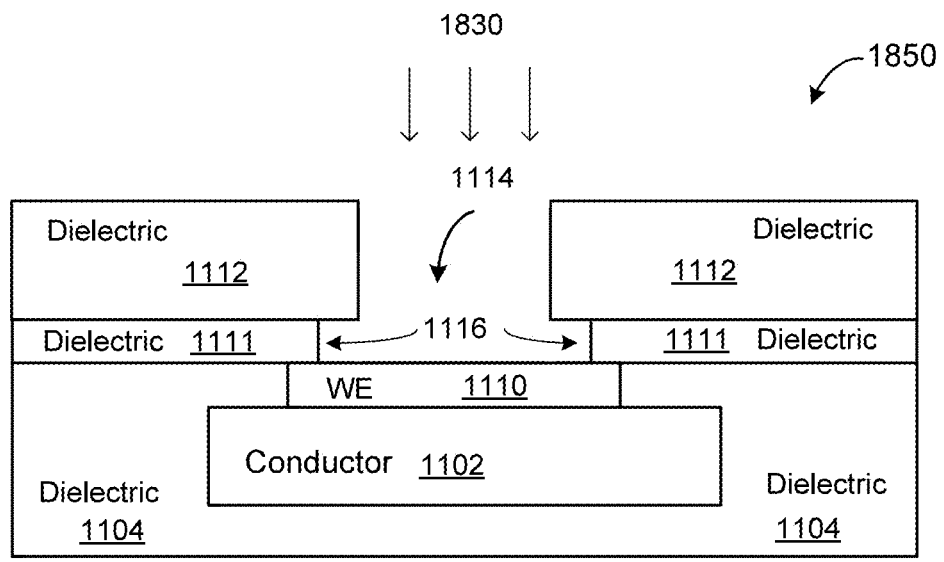

FIGS. 18A and 18B are cross-sectional views of representative nanopore device structures that are suitable for the surface treatment. FIG. 18A illustrates a nanopore device 1800 similar to devices depicted in FIG. 17H, or 13G, where polishing may or may not be used to form the working electrode. FIG. 18B illustrates a nanopore device 1850 similar to devices depicted in FIG. 7 or 11F, where a polishing method may or may not be used to form the working electrode. In FIG. 18A, the components are identified with the same reference numerals as the corresponding components in FIG. 17H. In FIG. 18B, the components are identified with the same reference numerals as the corresponding components in FIG. 11F. In both FIGS. 18A and 18B, the arrows 1830 correspond to the application of the chemistry in the new surface treatment.

In some nanopore devices, a sacrificial layer, or protective layer, such as an oxide layer, can be formed over the electrode layer during device formation. The sacrificial layer can be removed by a wet etch process, for example, using a buffered oxide etch (BOE) etch. With this chemical, a longer etch time can be chosen to increase Titanium Nitride (TiN) electrode double-layer capacitance (Cdbl). The prolonged etch can result in undercut regions such as 1718 in FIG. 18A and 1116 in FIG. 18B. However, with the certain cladding structure in the nanopore device, excessive BOE etch can cause damage, such as etching into underlying passivation oxide and/or electrode seed layer.

A chemistry including a mixture of oxidizing nitric acid ($HNO_3$) and HF diluted in DI water can increase double-layer capacitance. In some embodiments, equal portions of nitric acid ($HNO_3$) and HF can be used. This treatment can increase double-layer capacitance by increasing the electrode porosity. $HNO_3$ can oxidize the metallic electrode, and HF can dissolve the metal oxide. This enhanced reaction allows for a more diluted concentration of HF, which in turn can suppress oxide etch rates. As an example, a nitric acid ($HNO_3$) and HF mixture, diluted in DI Water to 1:1:400 concentration (0.1% HF), has been found to increase TiN working electrode double layer capacitance, Cdl, by increasing TiN porosity, but with high etch selectivity to oxide. In other examples, HF concentrations of 0.05% to 10% can be used.

Figure 19:
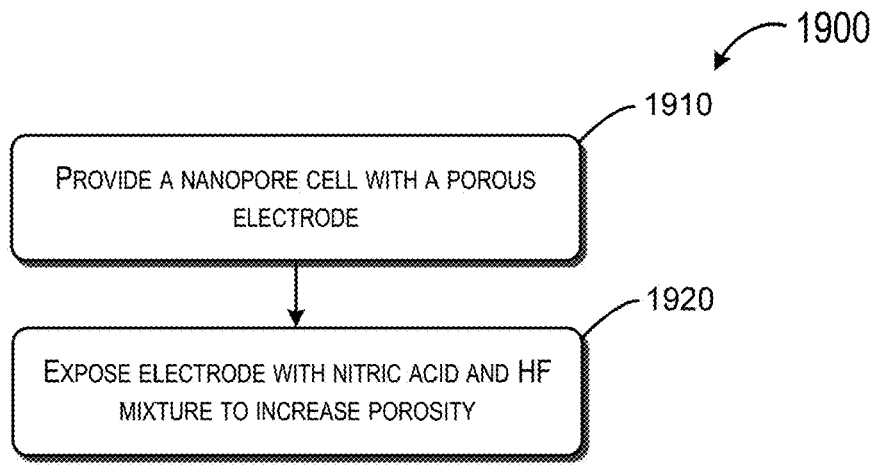
FIG. 19 is a flowchart illustrating a method of surface treatment for increasing porosity of a porous electrode in a nanopore device.

FIG. 19 is a flowchart illustrating a method of surface treatment for increasing porosity of a porous electrode in a nanopore device. At step 1910, a nanopore cell with a porous electrode is provided. Step 1910 is expanded further in FIG. 20. At step 1920, the electrode is exposed with a nitric acid and HF mixture to increase porosity. As described above, nitric acid ($HNO_3$) and HF can be diluted in DI water in various proportions can be used in the surface treatment.

Figure 20:
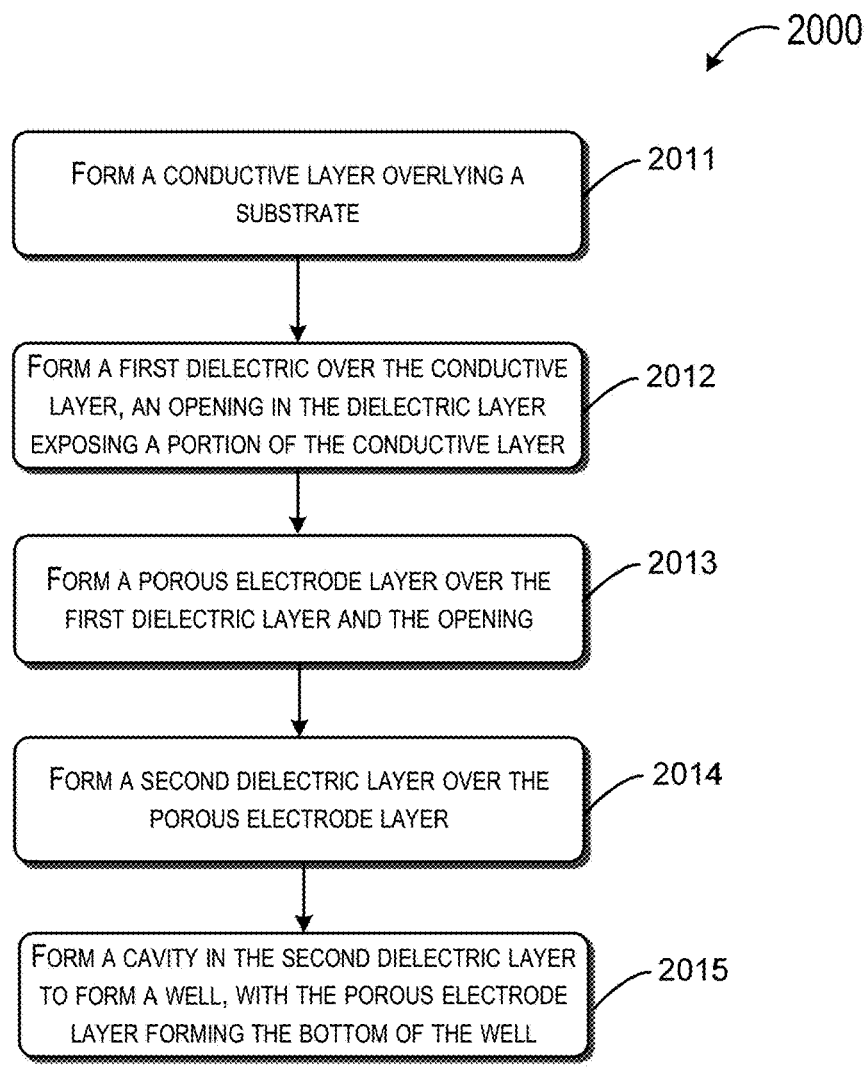
FIG. 20 is a flowchart illustrating a method for forming a nanopore device with a porous electrode.

FIG. 20 is a flowchart illustrating a method for forming a nanopore device with a porous electrode. Method 2000 in FIG. 20 can be used to form the nanopore device in step 1910 of FIG. 19 described above. Method 2000 includes the methods of forming nanopore devices described above in connection with FIGS. 7, 11A-11F, 13A-13G, 16A-16F, and 17A-17H, and the accompanying texts, which illustrate methods for forming various nanopore devices. Method 2000 can be briefly summarized as follows.

Method 2000 includes, at Step 2011, forming a conductive layer overlying a substrate. At Step 2012, a first dielectric is formed over the conductive layer. An opening in the dielectric layer exposing a portion of the conductive layer. More detail is provided in the description in connection with FIG. 7, Steps A and B, FIG. 13A, and FIG. 17A.

At Step 2013, a porous electrode layer is formed over the first dielectric layer and the opening. More detail is provided in the description in connection with FIG. 7, Step C. The embodiments can include several variations. For example, FIGS. 11A-11B illustrates forming a dielectric sacrificial layer over the porous electrode. FIG. 13B-13D illustrates forming a metallic sacrificial layer over the porous electrode, FIGS. 16B-16D illustrates forming a trapezoidal-shaped sacrificial layer over the porous electrode for forming a reentrant well. FIG. 17B-17E illustrates a process forming a sacrificial layer over the electrode layer using a non-polishing method.

At Step 2014, a second dielectric layer is formed over the porous electrode layer. More detail is provided in the description in connection with FIG. 7, Step D, FIG. 11C, FIG. 13E, FIG. 16E, and FIG. 17F.

At Step 2015, a cavity is formed in the second dielectric layer to form a well, with the porous electrode layer forming the bottom of the well. More detail is provided in the description in connection with FIG. 7, Step E, FIGS. 11D-11F, FIGS. 13F-13G, FIG. 16F, and FIGS. 17G-17H.

B. Device Evaluation

Figure 21:
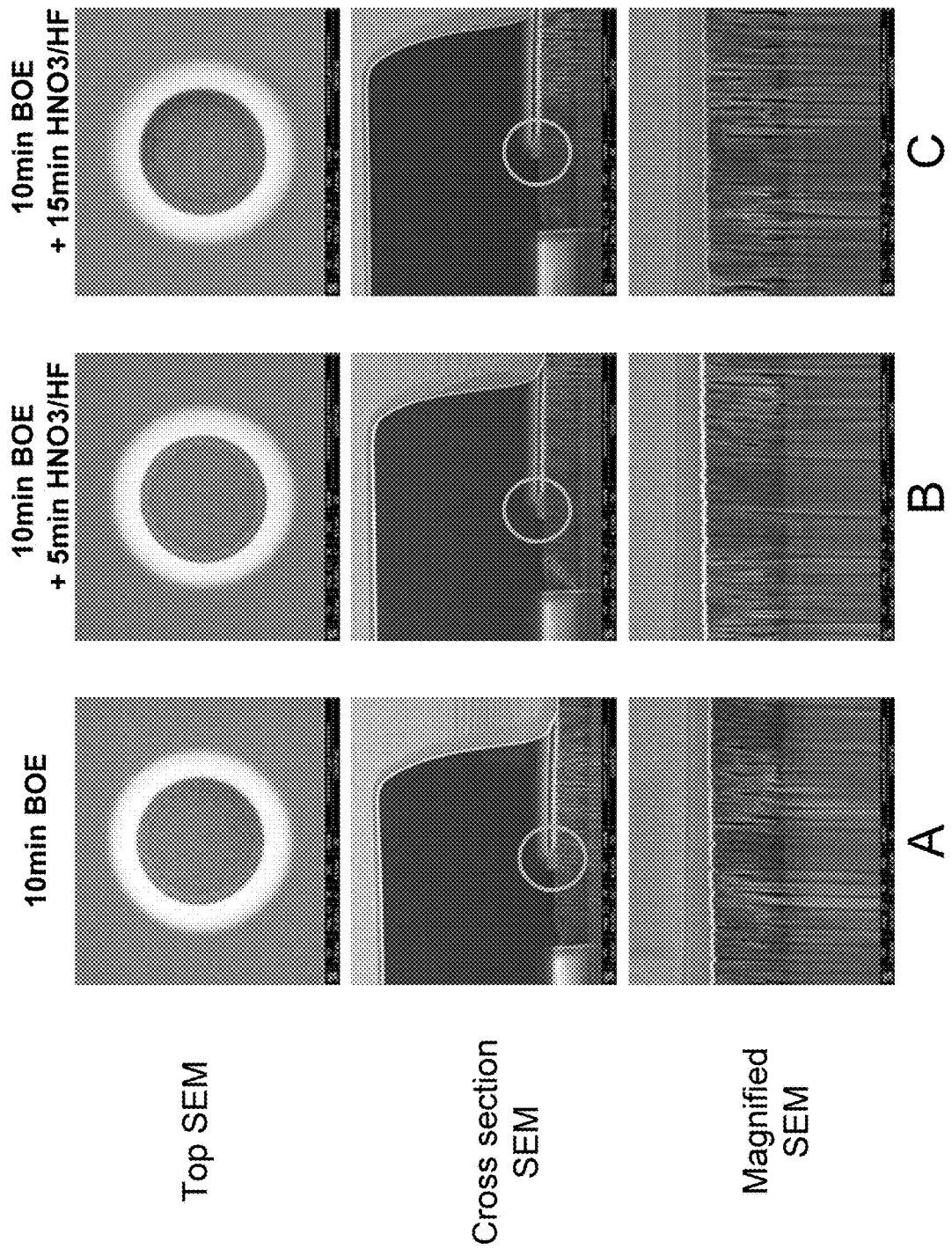
FIG. 21 provides SEM (scanning electron microscope) images illustrating the results of surface treatment for increasing the double layer capacitance of a nanopore device.

FIG. 21 provides SEM (scanning electron microscope) images illustrating the results of surface treatment for increasing the double layer capacitance of a nanopore device. Three nanopore devices, A, B, and C (such as device 1800 shown in FIG. 18A, device 1850 shown in in FIG. 18B, or device 1700 shown in FIG. 17H) were treated with the same amount of BOE (buffered oxide etch) for 10 minutes to remove the protective oxide film. The three devices were then treated with additional $HNO_3$/HF chemistry for different lengths of time. Device A received no additional $HNO_3$/HF treatment, device B received an additional five minutes of $HNO_3$/HF treatment, and device C received an additional 15 minutes of $HNO_3$/HF treatment.

The top row of SEM images in FIG. 21 contains top-down SEM images of the electrodes for device A, B, and C. It can be seen from magnified views of the top down SEM images that the porosity of the electrode increases with the increased time of the $HNO_3$/HF surface treatment. The increased electrode porosity is also confirmed from double layer capacitance measurements described in more detail below in connection with FIG. 22. The center row of SEM images in FIG. 21 contains cross-section SEM images of the electrodes. The circles in the center row of SEM images show that no change to the residual protective oxide is observed from the cross-section images, highlighting the high etch selectivity this treatment has on oxide. The high etch selectivity allows longer treatment, which increases porosity. The bottom row of SEM images in FIG. 21 contains magnified cross-section SEM images of the electrodes showing more details of the porous working electrode.

In some cases, prolonged treatment in the $HNO_3$/HF mixture may attack the titanium (Ti) layer, which is used as the seed material for the TiN working electrode. However, this issue can be mitigated by choosing a seed material with high resistance to HF, such as tungsten (W) or chromium (Cr).

Figure 22:
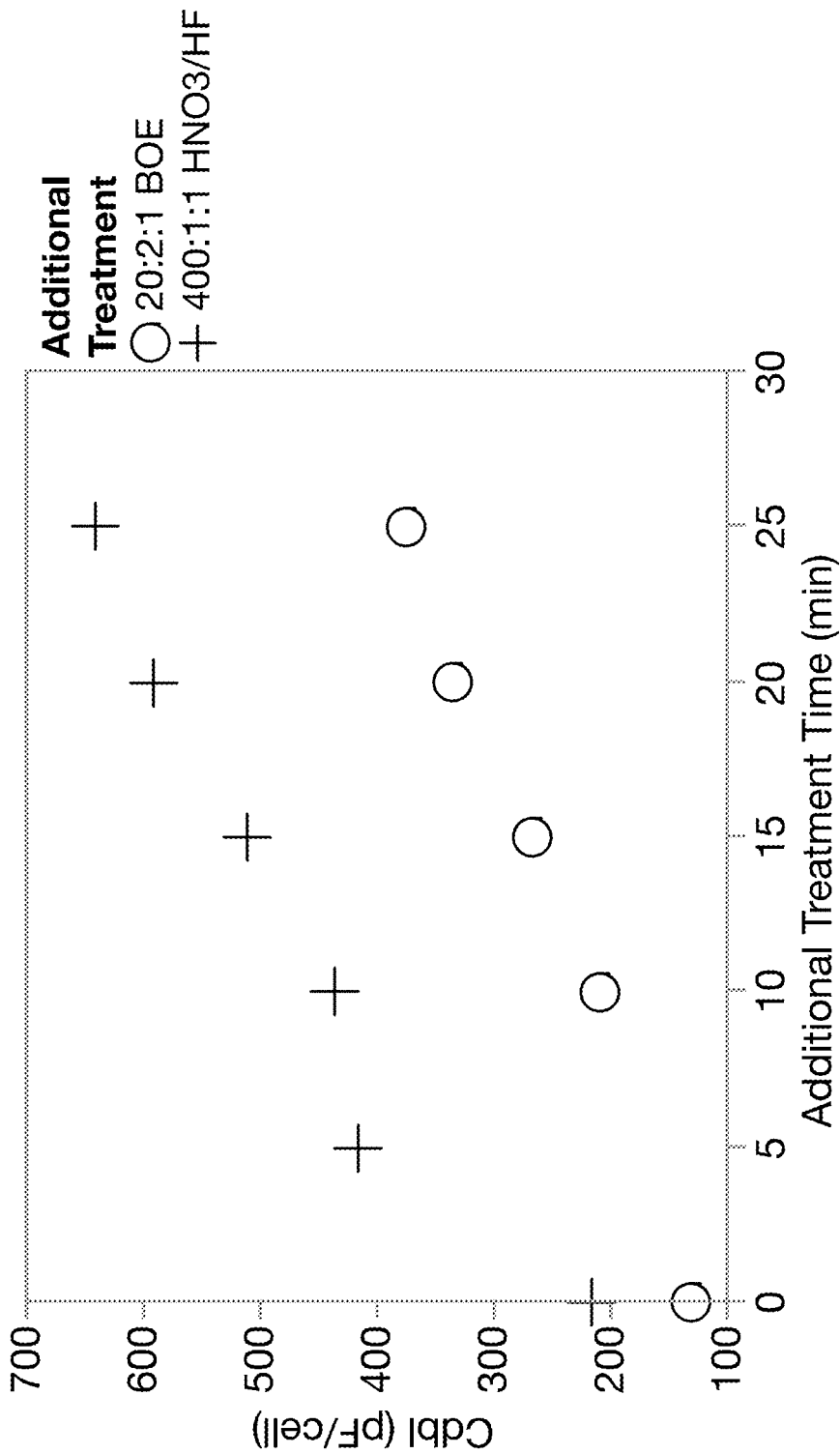
FIG. 22 is a diagram illustrating an increase in the double layer capacitance with additional surface treatment time.

FIG. 22 is a diagram illustrating an increase in the double layer capacitance with additional surface treatment time. Two nanopore devices, such as device 1800 shown in FIG. 18A, were used in this experiment. Both devices had an initial wet etch process of 10 minutes in 20:2:1 BOE to remove protective oxide (cap layer). In FIG. 22, the circles illustrate the double layer capacitance Cdbl for the first device, which had an initial double layer capacitance of about 120 pF/cell about. After an additional 10-minute treatment in 20:2:1 BOE, the double layer capacitance for the first device increased to about 200 pF/cell. After a 20-minute additional treatment in 20:2:1 BOE, the double layer capacitance increased to about 320 pF/cell.

In FIG. 22, the crosses illustrate the double layer capacitance Cdbl for the second device, which had an initial double layer capacitance of about 210 pF/cell after the removal of protective oxide (cap layer) using a wet etch process of 10 minutes in 20:2:1 BOE. After an additional 10-minute treatment in 400:1:1 $HNO_3$/HF, the double layer capacitance increased to about 430 pF/cell. Further, after a 20-minute additional treatment in 400:1:1 $HNO_3$/HF, the double layer capacitance increases to about 600 pF/cell. The variation in the initial double layer capacitances of the two devices are due to device variations.

As described above, continued treatment in 20:2:1 BOE poses the risk of over-etching the underlying dielectric layer (field oxide) in the device. However, treatment in 400:1:1 $HNO_3$/HF is shown to effectively increase the double-layer capacitance of the porous electrode without causing excessive oxide loss in the underlying structures.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Where a range of values is provided, it is understood that each intervening value, to the tenth of the unit of the lower limit unless the context clearly dictates otherwise, between the upper and lower limits of that range, is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods.

Several embodiments of the invention are described above. However, it will be recognized by those of skill in the art that various modifications, alternative constructions, and equivalents may be used without departing from the spirit of the invention. For example, even though a polyimide layer is used as an example of a hydrophobic material for well formation in the above description, other organic material having hydrophobic surface properties, such as CYTOP, which is an amorphous fluoropolymer, may also be used in other embodiments. Moreover, besides silicon oxide, other dielectric materials having proper etch selectivity and process compatibility can also be used to form the sacrificial layer, for example, silicon nitride, zirconium oxide, and hafnium oxide, etc. Additionally, a number of well-known processes and elements have not been described in order to avoid unnecessarily obscuring the present invention. Additionally, details of any specific embodiment may not always be present in variations of that embodiment or may be added to other embodiments.

All patents, patent applications, publications, and descriptions mentioned herein are incorporated by reference in their entirety for all purposes. None is admitted to be prior art.

What is claimed is:

1. A nanopore cell, comprising:
    a substrate;
    a conductive layer disposed overlying a top portion of the substrate;
    a first dielectric layer overlying the conductive layer, the first dielectric layer having an opening exposing a portion of the conductive layer;
    an electrode layer disposed in the opening of the first dielectric layer, the electrode layer having an overhang portion extending over the first dielectric layer;
    a second dielectric layer disposed on the first dielectric layer;
    a cavity in the second dielectric layer, the cavity exposing at least a portion of the electrode layer, the cavity including an undercut portion of the second dielectric layer above the overhang portion of the electrode layer; and
    a well formed by the cavity, the well having a bottom base formed by a top surface of the electrode layer and well sidewalls formed by the second dielectric layer.

2. The nanopore cell of claim 1, wherein the electrode layer comprises porous TiN (titanium nitride).

3. The nanopore cell of claim 1, wherein the second dielectric layer comprises polyimide.

4. The nanopore cell of claim 1, wherein the second dielectric layer comprises an organic material.

5. The nanopore cell of claim 1, wherein the first dielectric layer comprises an oxide layer.

6. The nanopore cell of claim 1, wherein the overhang portion has a length in a range of 0.3 µm to 5 µm.

7. The nanopore cell of claim 1, wherein the undercut portion has a length in a range of 0.2 µm to 5 µm.

8. The nanopore cell of claim 1, wherein the well has a width in a range of 1 µm to 10 µm and a depth in a range of 1 µm to 4 µm.

* * * * *